(12) United States Patent
Kaeppler et al.

(10) Patent No.: US 10,858,664 B2
(45) Date of Patent: Dec. 8, 2020

(54) MODIFYING FLOWERING TIME IN MAIZE

(71) Applicant: Wisconsin Alumni Research Foundation, Madison, WI (US)

(72) Inventors: Shawn Kaeppler, Oregon, WI (US); Natalia de Leon, Middleton, WI (US); Jillian M. Foerster, Des Moines, IA (US); German Muttoni, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1169 days.

(21) Appl. No.: 14/296,352

(22) Filed: Jun. 4, 2014

(65) Prior Publication Data

US 2014/0366213 A1 Dec. 11, 2014

Related U.S. Application Data

(60) Provisional application No. 61/831,561, filed on Jun. 5, 2013.

(51) Int. Cl.
*C12N 15/82* (2006.01)
*C07K 14/415* (2006.01)

(52) U.S. Cl.
CPC .......... *C12N 15/827* (2013.01); *C07K 14/415* (2013.01)

(58) Field of Classification Search
None
See application file for complete search history.

(56) References Cited

U.S. PATENT DOCUMENTS

2007/0192889 A1* 8/2007 La Rosa ............... C07K 14/415 800/278
2016/0017349 A1* 1/2016 Ayele ................. C12N 15/8218 800/285

OTHER PUBLICATIONS

Messenguy et al. Gene 316 (2003): 1-21.*
Becker et al. Molecular phylogenetics and evolution 29.3 (2003): 464-489.*
Guo et al. (2004, Proc. Natl. Acad. Sci. USA 101: 9205-9210).*
Messenguy et al. Gene 316 (2003): 1-21. (Year: 2003).*
Guo et al. (2004, Proc. Natl. Acad. Sci. USA 101: 9205-9210). (Year: 2004).*
UniProt Accession B4FML1, entered Nov. 23, 2008. (Year: 2008).*
Kapazoglou et al. (BMC plant biology 12.1 (2012): 166). (Year: 2012).*
Greenup et al. (Plant Physiology 153.3 (2010): 1062-1073). (Year: 2010).*
Jung et al. (Trends in plant science 14.10 (2009):563-573). (Year: 2009).*
"UniformMu_insertions_release_2.txt" retrieved from https://cur.maizegdb.org/UniformMu_insertions_release_2.txt on Mar. 23, 2020. (Year: 2020).*
https://urgi.versailles.inra.fr/gb2/gbrowse/Zea_mays_ZmB73_pub/?display_citation=UniformMU retrieved Mar. 23, 2020. (Year: 2020).*
https://www.maizegdb.org/uniformmu retrieved Mar. 23, 2020. (Year: 2020).*
Liang et al. (New Phytologist 221.4 (2019): 2335-2347). (Year: 2019).*
Buckler et al., "The Genetic Architecture of Maize Flowering Time," *Science* 325:714-718, 2009.
Chardon et al., "Genetic Architecture of Flowering Time in Maize as Inferred From Quantitative Trait Loci Meta-analysis and Synteny Conservation With the Rice Genome," *Genetics* 168:2169-2185, 2004.
Chen et al., "PICARA, an Analytical Pipeline Providing Probabilistic Inference about A Priori Candidates Genes Underlying Genome-Wide Association QTL in Plants," *PLoS One* 7:e46596, 2012.
Hirsch et al., "Insights into the Maize Pan-Genome and Pan-Transcriptome," *Plant Cell* online publication Jan. 31, 2014.
Huijser et al., "The control of developmental phase transitions in plants," *Development* 138:4117-29, 2011.
Jung et al., "Flowering time control and applications in plant breeding," *Trends Plant Sci.*, 14(10):563-73, 2009.
Kane et al., "TaVRT-2, a Member of the StMADS-11 Clade of Flowering Repressors, is Regulated by Vernalization and Photoperiod in Wheat," *Plant Physiol.* 138:2354-63. 2005.
Kikuchi et al., "PnMADS1, encoding an StMADS11-clade protein, acts as a repressor of flowering in *Pharbitis nil*," *Physiol Plant* 133:786-93, 2008.
Salvi et al., "Conserved noncoding genomic sequences associated with a flowering-time quantitative trait locus in maize," *PNAS* 104(27):11376-81, 2007.
Sentoku et al., "OsMADS22, an STMADS11-like MADS-box gene of rice, is expressed in non-vegetative tissues and its ectopic expression induces spikelet meristem indeterminacy," *Mol. Genet. Genomics* 273:1-9, 2005.

(Continued)

*Primary Examiner* — Charles Logsdon
(74) *Attorney, Agent, or Firm* — Dentons US LLP

(57) ABSTRACT

The present invention provides compositions and methods for modulating the reproductive transition in plants, such as grasses (e.g., maize). In particular, the invention provides methods for enhancing agronomic properties in plants by modulating expression of GRMZM2G171650 (zmm22) or homologs thereof. Modulation of expression of one or more additional genes which affect reproductive transition such as zagl1, in conjunction with such modulation of expression is also contemplated. Nucleic acid constructs for down-regulation of GRMZM2G171650 are also contemplated, as are transgenic plants, and products produced therefrom, that demonstrate altered development such as extended flowering time and display associated phenotypes such as enhanced yield of vegetative biomass, improved digestibility, and increased disease resistance. Plants described herein may be used, for example, as improved forage or feed crops or in biofuel production.

5 Claims, 2 Drawing Sheets
Specification includes a Sequence Listing.

(56) References Cited

OTHER PUBLICATIONS

Xu et al., "The Genetic Architecture of Flowering Time and photoperiod Sensitivity in Maize as Revealed by QTL Review and Meta Analysis," *J. Integr. Plant Biol.* 54(6):358-73, 2012.

Zhao et al., "MADS-box genes of maize: frequent targets of selection during domestication," *Genet. Res., Camb.* 93:65-75, 2011.

\* cited by examiner

MODIFYING FLOWERING TIME IN MAIZE

CROSS REFERENCE TO RELATED APPLICATIONS

This application claims the benefit of U.S. Provisional Application No. 61/831,561, filed Jun. 5, 2013, herein incorporated by reference in its entirety.

STATEMENT REGARDING FEDERALLY SPONSORED RESEARCH OR DEVELOPMENT

This invention was made with government support under DE-FC02-07ER64494 awarded by the US Department of Energy. The government has certain rights in the invention.

INCORPORATION OF SEQUENCE LISTING

The sequence listing that is contained in the file named WARF105US_ST25.txt, which is 64 KB (measured in MS-Windows) and was created on May 12, 2014, is filed herewith by electronic submission and incorporated herein by reference.

BACKGROUND OF THE INVENTION

Field of the Invention

The invention relates to methods and compositions for altering the timing of the vegetative to reproductive phase of plants.

Description of Related Art

The timing of developmental progression affects fitness of individuals within a species thereby allowing adaptation to new environments. Two key events in plant development include the juvenile to adult vegetative and the vegetative to floral transitions. Substantial natural phenotypic variation exists for these traits in plants, facilitating evolution and adaptation to new environments, crop domestication and dispersal, and cultivar improvement within crop species. Juvenile and adult vegetative tissues in grasses differ dramatically in anatomy, biochemical composition, and in their ability to withstand biotic and abiotic stresses. Juvenile plants cannot flower and are capable of only vegetative growth. Juvenile leaf tissue further has inherent resistance to specific abiotic stresses such as cold and drought, is generally less recalcitrant when used for processing for biofuels, and may be more digestible when used as feed. Researchers have identified certain parameters such as age, leaf number, and certain growth conditions as playing a role in the maturation of juvenile plant tissue to adult plant tissue. However, the genetic triggers controlling the vegetative to floral transition in plants have not been well understood.

SUMMARY OF THE INVENTION

In one aspect, the present invention provides a polynucleotide molecule including a sequence selected from the group consisting of: (a) a sequence having at least 90% sequence identity to a sequence selected from the group consisting of SEQ ID NO:1, SEQ ID NO:2, SEQ ID NO:3, SEQ ID NO:4, SEQ ID NO:5, and SEQ ID NO:6, wherein the sequence encodes a polypeptide that regulates flowering time in maize; (b) a sequence encoding a polypeptide at least 90% identical to a polypeptide selected from the group consisting of SEQ ID NO:7, SEQ ID NO:8, SEQ ID NO:9, SEQ ID NO:10, and SEQ ID NO:11, wherein the polypeptide regulates flowering time in maize; (c) a sequence comprising a construct that includes all or a portion of the sequence selected from the group consisting of SEQ ID NO:1, SEQ ID NO:2, SEQ ID NO:3, SEQ ID NO:4, SEQ ID NO:5, and SEQ ID NO:6, and the reverse complement thereof, wherein transcription of the construct in maize suppresses the expression of the polypeptide selected from the group consisting of SEQ ID NO:7, SEQ ID NO:8, SEQ ID NO:9, SEQ ID NO:10, and SEQ ID NO:11; and (d) a sequence complementary to (a) or (b), wherein the polynucleotide molecule is operably linked to a heterologous promoter functional in plants. In one embodiment, the polynucleotide molecule comprises a sequence selected from the group consisting of SEQ ID NO:1, SEQ ID NO:2, SEQ ID NO:3, SEQ ID NO:4, SEQ ID NO:5, and SEQ ID NO:6.

In another aspect, the present invention provides a recombinant vector comprising a polynucleotide molecule comprising a sequence selected from the group consisting of: (a) a sequence having at least 90% sequence identity to a sequence selected from the group consisting of SEQ ID NO:1, SEQ ID NO:2, SEQ ID NO:3, SEQ ID NO:4, SEQ ID NO:5, and SEQ ID NO:6, wherein the sequence encodes a polypeptide that regulates flowering time in maize; (b) a sequence encoding a polypeptide at least 90% identical to a polypeptide selected from the group consisting of SEQ ID NO:7, SEQ ID NO:8, SEQ ID NO:9, SEQ ID NO:10, and SEQ ID NO:11, wherein the polypeptide regulates flowering time in maize; (c) a sequence comprising a construct that includes all or a portion of the sequence selected from the group consisting of SEQ ID NO:1, SEQ ID NO:2, SEQ ID NO:3, SEQ ID NO:4, SEQ ID NO:5, and SEQ ID NO:6, and the reverse complement thereof, wherein transcription of the construct in maize suppresses the expression of the polypeptide selected from the group consisting of SEQ ID NO:7, SEQ ID NO:8, SEQ ID NO:9, SEQ ID NO:10, and SEQ ID NO:11; and (d) a sequence complementary to (a) or (b), wherein the polynucleotide molecule is operably linked to a heterologous promoter functional in plants. In some embodiments, the recombinant vector includes at least one additional sequence chosen from the group consisting of: a regulatory sequence, a selectable marker, a leader sequence, and a terminator. In other embodiments, the additional sequence is a heterologous sequence with respect to said polynucleotide molecule. In yet other embodiments, the promoter is a developmentally-regulated promoter. In particular embodiments, the recombinant vector is defined as an isolated expression cassette.

In yet another aspect, the present invention provides a transgenic grass plant including a recombinant vector comprising a polynucleotide molecule comprising a sequence selected from the group consisting of: (a) a sequence having at least 90% sequence identity to a sequence selected from the group consisting of SEQ ID NO:1, SEQ ID NO:2, SEQ ID NO:3, SEQ ID NO:4, SEQ ID NO:5, and SEQ ID NO:6, wherein the sequence encodes a polypeptide that regulates flowering time in maize; (b) a sequence encoding a polypeptide at least 90% identical to a polypeptide selected from the group consisting of SEQ ID NO:7, SEQ ID NO:8, SEQ ID NO:9, SEQ ID NO:10, and SEQ ID NO:11, wherein the polypeptide regulates flowering time in maize; (c) a sequence comprising a construct that includes all or a portion of the sequence selected from the group consisting of SEQ ID NO:1, SEQ ID NO:2, SEQ ID NO:3, SEQ ID NO:4, SEQ ID NO:5, and SEQ ID NO:6, and the reverse complement thereof, wherein transcription of the construct in maize suppresses the expression of the polypeptide selected from the group consisting of SEQ ID NO:7, SEQ ID NO:8, SEQ ID NO:9, SEQ ID NO:10, and SEQ ID NO:11;

and (d) a sequence complementary to (a) or (b), wherein the polynucleotide molecule is operably linked to a heterologous promoter functional in plants. In other embodiments, the transgenic grass plant exhibits altered flowering time relative to an otherwise isogenic plant lacking the recombinant vector. In yet other embodiments, the altered flowering time includes lengthened flowering time relative to the otherwise isogenic plant. In some embodiments, the altered flowering time includes shortened flowering time relative to the otherwise isogenic plant. In other embodiments, the grass plant is a wheat, sorghum, maize, rice, switchgrass or barley plant.

In certain aspects, the invention also provides a seed or cell of such a transgenic grass plant. In some embodiments, the seed or cell includes the recombinant vector.

In a particular aspect, the present invention provides a method of altering the flowering time of a maize plant including modulating the expression of gene GRMZM2G171650 in the plant. In certain embodiments, the method includes expressing a recombinant vector including a polynucleotide molecule comprising a sequence selected from the group consisting of: (a) a sequence having at least 90% sequence identity to a sequence selected from the group consisting of SEQ ID NO:1, SEQ ID NO:2, SEQ ID NO:3, SEQ ID NO:4, SEQ ID NO:5, and SEQ ID NO:6, wherein the sequence encodes a polypeptide that regulates flowering time in maize; (b) a sequence encoding a polypeptide at least 90% identical to a polypeptide selected from the group consisting of SEQ ID NO:7, SEQ ID NO:8, SEQ ID NO:9, SEQ ID NO:10, and SEQ ID NO:11, wherein the polypeptide regulates flowering time in maize; (c) a sequence comprising a construct that includes all or a portion of the sequence selected from the group consisting of SEQ ID NO:1, SEQ ID NO:2, SEQ ID NO:3, SEQ ID NO:4, SEQ ID NO:5, and SEQ ID NO:6, and the reverse complement thereof, wherein transcription of the construct in maize suppresses the expression of the polypeptide selected from the group consisting of SEQ ID NO:7, SEQ ID NO:8, SEQ ID NO:9, SEQ ID NO:10, and SEQ ID NO:11; and (d) a sequence complementary to (a) or (b), wherein the polynucleotide molecule is operably linked to a heterologous promoter functional in plants. In other embodiments, expressing the recombinant vector results in over-expression of the GRMZM2G171650 gene. In yet other embodiments, expressing the recombinant vector suppresses the expression of the GRMZM2G171650 gene. In still other embodiments, the method includes mutagenizing the GRMZM2G171650 gene.

In one aspect, the present invention provides a method of obtaining a maize plant with a desired flowering time including introgressing a GRMZM2G171650 gene allele, that confers the desired flowering time, from a plant variety including the allele into a plant variety lacking the allele. In one embodiment, introgressing uses marker-assisted selection for the allele. In another embodiment, the method includes using the plant variety lacking the allele as a recurrent parent for at least about 2 to about 8 generations. In certain embodiments, the marker assisted selection comprises the use of a SNP marker. In some embodiments, the SNP marker is within gene GRMZM2G171650, GRMZM2G171622, or GRMZM2G082608. In other embodiments, the SNP marker is selected from the group consisting of position 158979657, 158982604, and 159007174 on maize chromosome 3.

In another aspect, the present invention provides a method of producing a plant commodity product including: (a) obtaining a transgenic plant including a recombinant vector; and (b) preparing the commodity product from the plant. In some embodiments, the recombinant vector includes a polynucleotide molecule comprising a sequence selected from the group consisting of: (a) a sequence having at least 90% sequence identity to a sequence selected from the group consisting of SEQ ID NO:1, SEQ ID NO:2, SEQ ID NO:3, SEQ ID NO:4, SEQ ID NO:5, and SEQ ID NO:6, wherein the sequence encodes a polypeptide that regulates flowering time in maize; (b) a sequence encoding a polypeptide at least 90% identical to a polypeptide selected from the group consisting of SEQ ID NO:7, SEQ ID NO:8, SEQ ID NO:9, SEQ ID NO:10, and SEQ ID NO:11, wherein the polypeptide regulates flowering time in maize; (c) a sequence comprising a construct that includes all or a portion of the sequence selected from the group consisting of SEQ ID NO:1, SEQ ID NO:2, SEQ ID NO:3, SEQ ID NO:4, SEQ ID NO:5, and SEQ ID NO:6, and the reverse complement thereof, wherein transcription of the construct in maize suppresses the expression of the polypeptide selected from the group consisting of SEQ ID NO:7, SEQ ID NO:8, SEQ ID NO:9, SEQ ID NO:10, and SEQ ID NO:11; and (d) a sequence complementary to (a) or (b), wherein the polynucleotide molecule is operably linked to a heterologous promoter functional in plants. In particular embodiments, the commodity product is grain, starch, seed oil, corn syrup, silage, meal, or protein.

BRIEF DESCRIPTION OF THE SEQUENCES

Figure 1A:
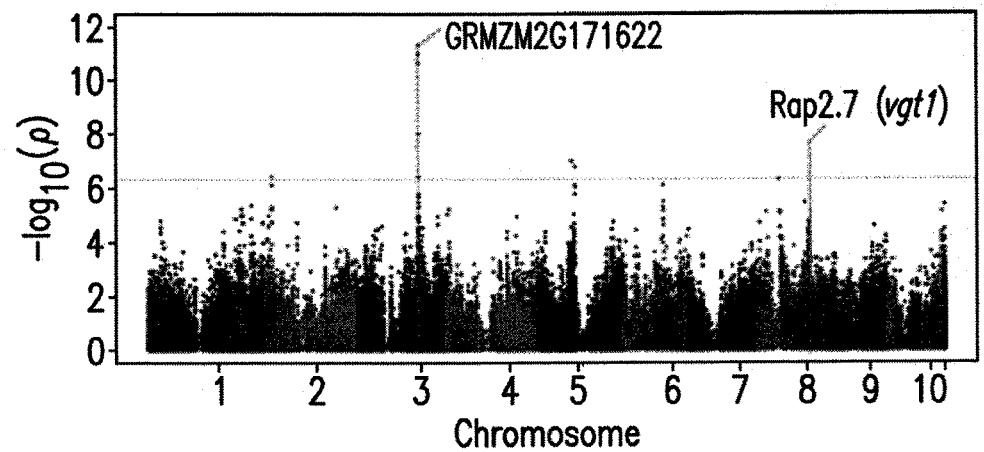
FIG. 1: Genome Wide Association Analysis (GWAS) for growing degree days to pollen shed. (A) Manhattan plot of GWAS results for growing degree days to pollen shed using single nucleotide polymorphism (SNP) markers, where genome-wide significance threshold (horizontal dashed line) was set using the simpleM method ($4.7 \times 10^{-7}$). (B) Manhattan plot of GWAS results using gene expression level as the dependent variable for growing degree days to pollen shed, where significance threshold was set using Bonferroni correction ($1.04 \times 10^{-6}$). (C) Linkage disequilibrium heat map between the most significant gene on chromosome 3 based on SNP markers, GRMZM2G171622, and candidate gene GRMZM2G171650, a MADS-box transcription factor; where asterisks=significant SNPs identified through GWAS.

SEQ ID NO:1 GRMZM2G171650 genomic nucleotide sequence from *Zea mays* B73.

SEQ ID NOs:2-6 GRMZM2G171650 cDNA isoform sequences from *Zea mays* B73.

SEQ ID NOs:7-11 GRMZM2G171650 translated sequences of SEQ ID NOs:2-6.

SEQ ID NO:12 GRMZM2G171650 homologous protein sequence from *Arabidopsis*.

SEQ ID NO:13 GRMZM2G171650 homologous protein sequence from *Oryza*.

SEQ ID NO:14 GRMZM2G171650 homologous protein sequence from *Brachypodium*.

SEQ ID NO:15 GRMZM2G171650 homologous protein sequence from *Sorghum*.

SEQ ID NO:16 GRMZM2G171650 homologous protein sequence from *Populus*.

SEQ ID NO:17 GRMZM2G171650 homologous protein sequence from *Vitis*.

SEQ ID NO:18 GRMZM2G700665 (Rap2.7) cDNA sequence from *Zea mays* B73.

SEQ ID NO:19 GRMZM2G700665 (Rap2.7) cDNA sequence from *Zea mays* B73.

SEQ ID NO:20 GRMZM2G700665 (Rap2.7) cDNA sequence from *Zea mays* B73.

DETAILED DESCRIPTION OF THE INVENTION

The present invention provides a gene, and methods for its use, to modulate the time to flowering. By modulate is meant to either hasten or delay the number of days or accumulated heat units required for a plant to flower. A plant or product comprising a recombinant DNA construct comprising such a gene may exhibit improved properties relating to, for instance, biofuel production and/or processing, use as animal feed, and resistance to a plant pest or plant disease, and is also an aspect of the invention. Seed of such a plant is also an aspect of the invention.

Plants must transition from the juvenile to adult vegetative phase prior to flowering, as plants acquire reproductive competence during this transition. During the vegetative to reproductive transition, the shoot apical meristem becomes an inflorescence meristem. The timing of this transition is important for basic plant development, survival, and fitness, and it is significantly correlated with several agronomically important traits.

Flowering time has been studied in *Arabidopsis* as well as grasses such as maize, rice, and wheat and is controlled by several endogenous factors and the environment. Several of the key genetic components controlling the juvenile to adult vegetative phase change are also crucial in the vegetative to reproductive transition. Some genes controlling maize flowering time have been identified through association studies, nested association mapping (NAM), and Quantitative Trait Loci (QTL) meta-analyses. To date, only one major maize flowering time QTL has been cloned, Vegetative to generative transition1 (Vgt1).

The present invention provides a MADS-box transcription factor, GRMZM2G171650 (zmm22) on chromosome 3, for controlling flowering time. GRMZM2G171650 is a gene of previously unknown function in corn (i.e., maize) which was identified through evaluation of the maize seeding pan transcriptome by mapping single nucleotide polymorphisms (SNPs) correlating to phenotypes of early or late flowering, and functions as a trigger of juvenile to adult growth phase change. Protein alignments show that this gene encodes a StMADS-11 like transcription factor and this clade of proteins act as a repressor of flowering in several species including wheat and rice. MADS-box genes are involved in floral organ identity and patterning. In addition, MADS-box genes have been shown to be frequent targets of selection during domestication and cultivar improvement. Modulating, such as disrupting, the expression of GRMZM2G171650 can alter, such as extend, the temporal duration during which a plant is in a juvenile phase of growth. Homologs of GRMZM2G171650 were identified in other plant species such as *Arabidopsis*, rice (*Oryza sativa*), *Brachypodium*, sorghum (*Sorghum bicolor*), poplar, and grapevine, among others; see exemplary sequence database accession numbers AT4G22950.1, LOC_Os01g69850.1, Bradi2g59190.1, Sb03g044170.1, POPTR_0014s07020.1, and GSVIVT00027579001, respectively (SEQ ID NOs:12-17). Therefore, this effect may be seen in other plants, such as monocotyledonous plants like grass plants (e.g., members of the Poaceae such as maize, rice sorghum, or switchgrass), as well as dicotyledonous plants. Thus, in particular embodiments, the invention provides compositions and methods for modulating expression of GRMZM2G171650 found on maize chromosome 3, or homologs thereof, in order to alter the timing of reproductive phase change in maize, rice, sorghum, switchgrass, or other plants.

In one aspect, the present invention provides methods for introducing into a plant a polynucleotide molecule provided herein to modify the flowering time of the plant. In one non-limiting example, the plant is maize and the flowering time is shortened or lengthened relative to a maize plant lacking the polynucleotide molecule. The ability to generate such a plant, or cell derived therefrom, depends on introducing the polynucleotide molecule using transformation and expression vectors or cassettes described herein.

In one aspect, the present invention provides a method for obtaining a maize plant with a desired flowering time by introgressing an allele of GRMZM2G171650, that confers the desired flowering time, from a plant variety possessing the allele into a plant variety lacking the allele. In certain embodiments, the introgression is accomplished using marker-assisted selection.

I. Nucleic Acids, Polypeptides and Plant Transformation Constructs

Certain embodiments of the present invention concern polynucleotide sequences comprising a GRMZM2G171650 coding sequence. Exemplary coding sequences for use with the invention include SEQ ID NO: 1 and SEQ ID NO:2, which encodes the polypeptide of SEQ ID NO:1. Constructs may also be designed that are complementary to all or part of the promoter and other control regions, exons, introns or even exon-intron boundaries of a gene.

The invention provides a nucleic acid sequence identical over its entire length to each coding sequence provided herein. The invention further provides a nucleic acid sequence displaying at least 90%, 95%, or 99% identity over its entire length to the full length, or a fragment, of the coding sequences provided herein. The invention also provides the coding sequence for a polypeptide or a fragment thereof, as well as the coding sequence for the polypeptide or a fragment thereof in a reading frame with other coding sequences, such as those encoding a leader or secretory sequence, a pre-, pro-, or prepro-protein sequence. The nucleic acid can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of a fused polypeptide. Nucleic acids of the present invention also include nucleic acids comprising a structural gene and the naturally associated sequences that control gene expression.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods. Computer programs can be used to determine "identity" between two sequences these programs include but are not limited to, GCG; suite of BLAST programs, three designed for nucleotide sequences queries (BLASTN, BLASTX, and TBLASTX) and two designed for protein sequence queries (BLASTP and TBLASTN). The BLASTX program is publicly available from NCBI and other sources (BLAST Manual, Altschul, S., et al., NCBI NLM NIH, Bethesda, Md. 20894; Altschul, S., et al., *J. Mol. Biol.* 215:403-410, 1990). The well known Smith Waterman algorithm can also be used to determine identity.

Parameters for polypeptide sequence comparison include the following: Algorithm: Needleman and Wunsch (*J. Mol. Biol.*, 48:443-453, 1970); Comparison matrix: BLOSUM62 from Hentikoff and Hentikoff, (*PNAS,* 89:10915-10919, 1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

The present inventors have identified the gene termed GRMZM2G171650 that impacts the time of flowering. Marker assisted breeding as well as methods of genetic modification may thus be used to introduce or introgress this gene, specific alleles thereof, or a modified version of this gene, or the described linkage group, into a plant to alter the timing of the juvenile to adult growth transition to achieve agronomic improvement. In certain embodiments of the invention, the process for producing such plants or lines comprises introducing a recombinant copy of GRMZM2G171650 or a variant thereof, into a plant. In other embodiments, the method comprises introgressing at least one chromosomal locus mapping to a QTL bounded by SNP markers at position 158979657 (G→C), 158982604 (G→T), and 159007174 (G→T) maize chromosome 3 into a plant. In other embodiments the function of a gene controlling the vegetative to floral transition can be disrupted, allowing for shortened or extended vegetative growth.

Vectors used for plant transformation may include, for example, plasmids, cosmids, YACs (yeast artificial chromosomes), BACs (bacterial artificial chromosomes) or any other suitable cloning system, as well as fragments of DNA there from. Thus when the term "vector" or "expression vector" is used, all of the foregoing types of vectors, as well as nucleic acid sequences isolated there from, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes.

II. Antisense and RNAi Constructs

A polynucleotide construct of the present invention may comprise a sequence for expression of an antisense RNA or dsRNA, such as siRNA or miRNA, which modulates expression of a GRMZM2G171650 coding sequence. By "modulates expression" is meant an increase or a decrease in such expression. Techniques for RNAi are well known in the art. Antisense and RNAi treatments thus represent one way of altering agronomic characteristics in accordance with the invention (e.g., by down regulation of a GRMZM2G171650 coding sequence). In particular, constructs comprising a GRMZM2G171650 coding sequence, including fragments thereof, in antisense orientation, or combinations of sense and antisense orientation, may be used to decrease or effectively eliminate the expression of a GRMZM2G171650 coding sequence in a plant and to alter agronomic characteristics (e.g., timing of the vegetative to reproductive phase). Accordingly, each of these may be used to "knockout" the function of a GRMZM2G171650 coding sequence or homologous sequences thereof.

III. Genetic Transformation

Suitable methods for transformation of plant or other cells for use with the current invention are believed to include virtually any method by which DNA can be introduced into a cell, such as by direct delivery of DNA such as by PEG-mediated transformation of protoplasts. These methods and their use are well known in the art.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, MS media may be modified by including further substances such as growth regulators. Examples of such growth regulators are dicamba and 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, then transferred to media conducive to maturation of embryoids. Cultures are transferred as needed on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at a suitable temperature, for instance about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and northern blotting and PCR; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Very frequently the expression of a gene product is determined by evaluating the phenotypic results of its expression. These assays also may take many forms including but not limited to analyzing changes in the chemical composition, morphology, or physiological properties of the plant. Morphological changes may include the presence of known floral structures such as immature or mature ears and tassels. Most often changes in response of plants or plant parts to imposed treatments are evaluated under carefully controlled conditions termed bioassays.

The present invention provides for a seed of a plant capable of producing a plant having an altered period of time from planting to flowering. In one aspect, the plant can be an open-pollinated variety, a hybrid parent inbred line, or a male sterile line. In another aspect, the invention provides seed of a plant capable of producing a plant having altered time to flower.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

In yet another aspect, tissue culture of the plants described herein relates to the culture of protoplasts, calli, or plant cells, that are isolated from, or present in, intact parts of the plants described herein.

Once plants are produced which display an enhanced (e.g., extended or shortened flowering time) the plants can be cultivated in accordance with conventional procedures, including via tissue culture and by sexual reproduction. The seeds resulting from sexual reproduction can be recovered and planted or otherwise grown as a means of propagation. Plants may also be obtained through asexual reproduction. Protoplast or propagules (e.g., cuttings, scions or rootstocks) can be recovered from plants or parts thereof and may be employed to propagate additional plants.

One aspect of the invention relates to vegetative tissues, including tissues harvested, dried, or otherwise processed, biomass produced by a plant having a genome that comprises at least one genetic locus giving rise to an altered time to flowering.

The present invention also provides progeny of plants displaying extended or shortened flowering time. As used herein, progeny include not only, without limitation, the products of any cross (be it a backcross or otherwise) between two plants, but all progeny whose pedigree traces back to the original cross.

One embodiment of the present invention provides for a plant that contains a genetic marker linked to one or more loci allowing for altered flowering time. By "altered flowering time locus" is meant a locus that contributes to such altered flowering time either alone or in combination with one more other locus.

IV. Definitions

As used herein, a "desirable trait" or "desirable traits" include, but are not limited to: increased vegetative growth, improved vegetative yield, improved digestibility when used as animal feed, and improved processing of biomass for preparation of, for instance, biofuel, among others.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, dsRNA, a transcriptional profile, and a methylation pattern may comprise polymorphisms. In addition, the presence, absence, or variation in copy number of the preceding may comprise a polymorphism.

As used herein, "genotype" is the actual nucleic acid sequence at a locus in an individual plant. As used herein, "phenotype" means the detectable characteristics (e.g., timing of production of leaves displaying adult morphological characteristics, such as the presence of reproductive inflorescence) of a cell or organism which can be influenced by genotype.

As used herein, linkage of two nucleic acid sequences, including a nucleic acid marker sequence and a nucleic acid sequence of a genetic locus imparting a desired trait may be genetic or physical or both. In one aspect of the invention, the nucleic acid marker and genetic locus conferring an altered flowering time are genetically linked, and exhibit a LOD score of greater than 2.0, as judged by interval mapping for the trait based on maximum likelihood methods described by Lander and Botstein (*Genetics,* 121:185-199, 1989), and implemented in the software package MAPMAKER (e.g., Lander et al., *Genomics* 1:174-181, 1987; default parameters). Alternatively, other software such as QTL Cartographer v1.17 (Basten et al., Zmap-a QTL cartographer. In: Proceedings of the 5th World Congress on Genetics Applied to Livestock Production Computing Strategies and Software, edited by C. Smith, J. S. Gavora, B. Benkel, J. Chesnais, W. Fairfull, J. P. Gibson, B. W. Kennedy and E. B. Burnside. Volume 22, pages 65-66. Organizing Committee, 5th World Congress on Genetics Applied to Livestock Production, Guelph, Ontario, Canada, 1994; and Basten et al., QTL Cartographer, Version 1.17. Department of Statistics, North Carolina State University, Raleigh, N.C., 2004) may be used. Mapping of QTLs is well-described (e.g., WO 90/04651; U.S. Pat. Nos. 5,492,547, 5,981,832, 6,455,758; reviewed in Flint-Garcia et al. (*Ann. Rev. Plant Biol.*, 54:357-374, 2003, the disclosures of which are hereby incorporated by reference). In other embodiments, the marker and region conferring enhanced juvenile growth are genetically linked and exhibit a LOD score of greater than 3.0, or a LOD score of greater than 6.0, 9.0, 12.0, 15.0, or 18.0. In one embodiment, the marker and region contributing to such growth are genetically linked and exhibit a LOD score of between about 14 and about 20. When assigning the presence of a QTL, the LOD threshold score associated with a QTL analysis as described herein may be determined to be significant for instance at the 95% confidence level, or higher, such as at the 98% or 99% confidence level.

In another aspect, the nucleic acid marker is genetically linked at a distance of between about 0 and less than about 50 centimorgans (cM) to the locus of interest, e.g., a GRMZM2G171650 coding sequence. In other embodiments, the distance between the nucleic acid marker and the locus of interest is between about 0 and about 35 cM, or between about 0 and about 25 cM, or between about 0 and about 15 cM, or between about 0 and about 10 cM, or between about 0 and about 5 cM, including less than about 4, 3, 2 or 1 cM.

As used herein, two nucleic acid molecules are said to be capable of hybridizing to one another if the two molecules are capable of forming an anti-parallel, double-stranded nucleic acid structure. Conventional stringency conditions are described by Sambrook et al., *Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are known in the art, for example 6.0× sodium chloride/sodium citrate (SSC) at about 45° C., followed by a wash of 2.0×SSC at 50° C.; or can be found in Current Protocols in Molecular Biology, John Wiley & Sons, N.Y. (1989), 6.3.1-6.3.6. In some embodiments, hybridization conditions can be high, moderate or low stringency conditions. Preferred conditions include those using 50% formamide, 5.0×SSC, 1% SDS and incubation at 42° C. for 14 hours, followed by a wash using 0.2×SSC, 1% SDS and incubation at 65° C. Alternative wash conditions, such as of 0.15 M NaCl and 70° C. for 10 minutes may also be used.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C.; or 0.15 M NaCl and 70° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, isozyme markers, or microarray transcription profiles that are genetically linked to or correlated with the altered flowering time trait can be utilized (Walton, *Seed World* 22-29 (July, 1993); Burow and Blake, *Molecular Dissection of Complex Traits,* 13-29, Eds. Paterson, CRC Press, New York (1988)). Methods to isolate such markers and to design probes or primers useful in following the presence of such markers are known in the art. For example, locus-specific SSRs can be obtained by screening a genomic library for SSRs, sequencing of "positive" clones, designing primers which flank the repeats, and amplifying genomic DNA with these primers. Likewise, SNP markers may be identified as well.

The genetic linkage of marker molecules to the loci described herein can be established by a gene mapping model such as, without limitation, the flanking marker model, and the interval mapping, based on maximum likelihood methods described by Lander and Botstein (*Genetics,* 121:185-199, 1989), and implemented in the software packages MAPMAKER (Whitehead Institute for Biomedical Research, Cambridge Mass., USA) or QTL Cartographer (North Carolina State University, Bioinformatics Research Center) or the like.

A maximum likelihood estimate (MLE) for the presence of a marker is calculated, together with an MLE assuming no trait effect, to avoid false positives. A $\log_{10}$ of an odds ratio (LOD) is then calculated as: LOD=$\log_{10}$ (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein (1989), and further described by Ars and Moreno-Gonzalez, *Plant Breeding,*

Hayward, Bosemark, Romagosa (eds.) Chapman & Hall, London, pp. 314-331 (1993), and van Ooijen (*Heredity*, 83:613-624, 1999).

Selection of appropriate mapping or segregation populations is important in trait mapping. The choice of appropriate mapping population depends on the type of marker systems employed (Tanksley et al., Molecular mapping plant chromosomes. Chromosome structure and function: Impact of new concepts J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

Advanced breeding lines are collected from breeding programs. These are tested for their phenotype (e.g., an alteration in the timing of production of adult tissues), and genotyped for markers in the QTL intervals described herein. From these data, the smallest genetic interval is identified within each QTL containing the donor parent (DP) favorable allele among the tested lines.

Considerable genetic information can be obtained from a completely classified $F_2$ population using a codominant marker system (Mather, Measurement of Linkage in Heredity: Methuen and Co., (1938)). An $F_2$ population is the first generation of self or sib pollination after the hybrid seed is produced. Usually a single $F_1$ plant is self or sib pollinated to generate a population segregating for the nuclear-encoded genes in a Mendelian (1:2:1) fashion.

In contrast to the use of codominant markers, using dominant markers often requires progeny tests (e.g., $F_3$ or back cross self families) to identify heterozygous individuals. The information gathered can be equivalent to that obtained in a completely classified $F_2$ population. This procedure is, however, often prohibitive because of the cost and time involved in progeny testing. Progeny testing of $F_2$ individuals is often used in map construction where error is associated with single plant phenotyping, or when sampling the plants for genotyping affects the ability to perform accurate phenotyping, or where trait expression is controlled by a QTL. Segregation data from progeny test populations (e.g., $F_3$ or backcrossed or selfed families) can be used in trait mapping. Marker-assisted selection can then be applied to subsequent progeny based on marker-trait map associations ($F_2$, $F_3$), where linkage has not been completely disassociated by recombination events (i.e., maximum disequilibrium).

Recombinant inbred lines (RILs) (genetically related lines; usually >$F_5$) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g., Reiter et al., *PNAS*, 89:1477-1481, 1992). However, as the distance between markers becomes larger (i.e., loci become more independent), the information in RIL populations decreases dramatically when compared to codominant markers.

Backcross populations can be utilized as mapping populations. A backcross population (BC) can be created by crossing an $F_1$ to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., *PNAS*, 89:1477-1481, 1992).

Information obtained from backcross populations using either codominant or dominant markers is less than that obtained from completely classified $F_2$ populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci polymorphic between the parentals are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore et al., *PNAS*, 88:9828-9832, 1991). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing a plant displaying altered flowering time comprising: (a) crossing a plant displaying such growth with a plant lacking such growth to form a segregating population; (b) screening the population for amount and/or duration of juvenile growth; and (c) selecting one or more members of the population having said enhanced or extended juvenile growth.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new plant lines requires the development and selection of varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Descriptions of other breeding methods that are commonly used for different traits and crops can be found in one of several available reference books (e.g., Fehr, *Principles of Cultivar Development*, 1:2-3, 1987).

The present invention also provides for parts of the plants produced by a method of the present invention. Parts of grass plants, without limitation, include plant cells or parts of plant cells, seed, endosperm, meristem, flower, anther, ovule, pollen, fruit, flowers, stems, roots, stalks or leaves, scions, and root stocks. Plant parts also include the parts of a fruit. In one embodiment of the present invention, the plant part is a seed.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Association Mapping Analysis

GDD to silk, and GDD to pollen shed were measured on plants grown in a randomized complete block design (RCBD) with two replications across two years at the Arlington Agriculture Research Station in Wisconsin. GWAS was performed using a set of 199,619 SNPs with less than 60% missing data prior to imputation, termed the "GWAS SNP set." Imputation was performed using the population-based haplotype clustering algorithm of Scheet and Stephens, which was implemented via fastPHASE software (version 1.4) using the default settings for all parameters. GWAS was performed with 409 of the 503 original inbred lines for last leaf with juvenile wax and the flowering time traits, respectively, using a previously proposed mixed linear model (MLM), which is as follows: $y=X\beta+Wm+Qv+Zu+e$, where y is a vector of phenotypic observations, $\beta$ is a vector of fixed effects other than the SNP under testing (year and block effects), m is a vector of SNP (fixed effect), v is the vector of population effects (fixed effect), u is a vector of polygene background random effect (proportion of the breeding values not accounted for by the SNP marker), and e is a vector of residual effects. Q is an incidence matrix of principal component scores (eigenvectors) of marker-allele frequencies and X, W and Z are incidence matrices of ones and zeros relating y to $\beta$, m and u, respectively. The covariance of u is equal to KVA, where K is the kinship matrix that was estimated with a random set of SNPs according to the VanRaden method and VA is the additive variance estimated using restricted maximum likelihood (REML). The kinship matrix estimations and compressed mixed linear model 74 were performed with the GAPIT R package. Quality of the GWAS model fit was 21 evaluated with QQ plots. To account for multiple testing, without being overly conservative and control for the Type-II error rate, the simpleM method was used. This approach applies a Bonferroni correction to the actual number of independent tests, or the effective number of independent tests ($M_{eff}$), by considering the linkage disequilibrium between each pair of markers and applying principal component analysis to obtain the eigenvalues. The simpleM method has been shown to be an effective way to control the experiment-wise error rate in GWAS. In this study, the $M_{eff}$ was 93,807 (equal to the number of eigenvalues necessary to explain 99.5% of the variance). Including the SNPs discovered in RTAs (12,866), the Bonferroni threshold considering independent tests is 0.05/106,693 i.e., $4.7 \times 10^{-7}$ ($\alpha_e = 0.05$). The Bonferroni threshold for GWAS gene expression as the dependent variable based on the number of genes tested (48,137) was p-value of $1.04 \times 10^{-6}$.

Genetic Dissection of Flowering Time

Four different components of flowering time were measured on 409 inbreds of the diversity panel across two years with two replications per year: days to silk, days to pollen shed, growing degree days (GDD) to silk, and GDD to pollen shed. A large portion of the missing phenotypic data for flowering time was due to tropical lines not fully maturing in MidWest United States growing conditions. While the inbred lines within the diversity panel were selected to flower in Wisconsin (Hansey et al., Crop Science, 51:704-715, 2010), substantial phenotypic variation for flowering time was observed. Highly significant correlations were observed between days to silk, days to pollen shed, GDD to silk and GDD to pollen shed.

Figure 1B:
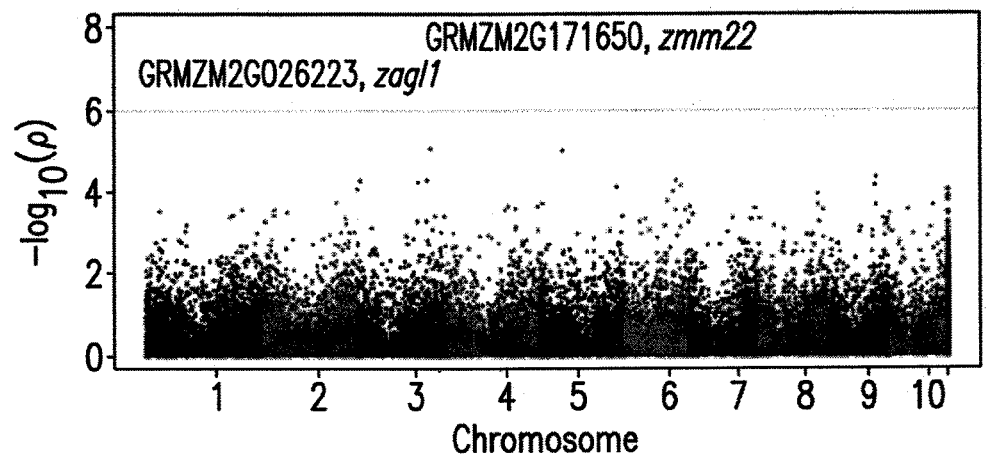
Figure 1C:
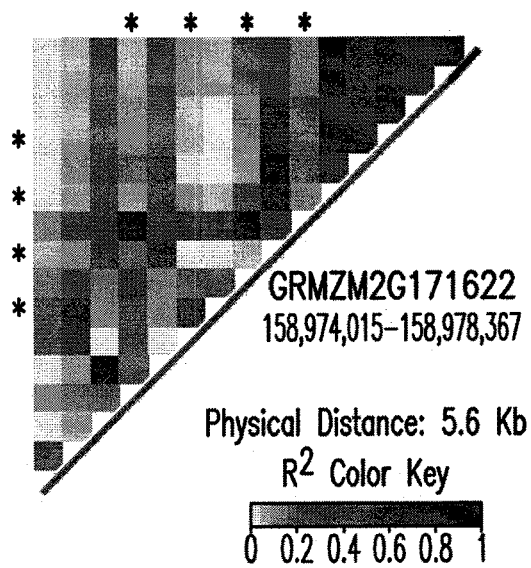

GWAS was performed for the flowering time traits using the GWAS SNP set and the parameters described above. Significant associations were detected for flowering time traits on chromosomes 2, 3, and 5 (FIG. 1A). Association mapping was also conducted using transcript abundance as the dependent variable for the flowering time traits with significant associations detected on chromosomes 1 and 3 (FIG. 1B). The most significant SNPs on chromosome 3, explaining over 6% of the phenotypic variation, were in a CBS-domain containing protein (GRMZM2G171622). In a previous analysis of the maize NAM population, a significant association in this region was also detected with a bootstrap posterior probability (BPP) of 0.4215. The gene adjacent to GRMZM2G171622 is annotated as a MADS-box transcription factor (GRMZM2G171650 [zmm22]) and contains only a single polymorphism within our data set and shows limited variation (minor allele frequency=0.18). This SNP within GRMZM2G171650 (zmm22) is in high LD with SNPs found in the CBS-domain containing protein (FIG. 1C), and GRMZM2G171650 (zmm22) was significant in the association analysis based on transcript abundance. Interestingly, zmm22, has previously been shown to be important in maize cultivar improvement (Zhao et al., Genet. Res. (Camb), 93:65-75, 2011) and this study provides evidence of its role in flowering time.

A gene on chromosome 1 identified based on transcript abundance, GRMZM2G026223 (zagl1) (FIG. 1B), is also a MADS-box transcription factor. GRMZM2G026223 contains only one polymorphism within the data set and shows very limited variation (minor allele frequency=0.08), which is consistent with the lack of diversity expected under a domestication selection sweep. These results demonstrate the value of using transcript abundance in GWAS, especially in detecting genes with limited SNP variation. ZmRap2.7, located on chromosome 8, and the non-coding region 70 kb upstream (VgtI) have been shown to be involved in flowering time control (Salvi et al., PNAS, 104:11376-81, 2007). SNPs identified within ZmRap2.7 were not significant in the diversity panel at the genome-wide multiple testing threshold but were significant when tested as a candidate gene (p-value=$3.47 \times 10^{-5}$).

For the flowering time traits, we found considerable overlap between our GWAS results and previous studies. The flowering time QTL on chromosome 3 detected in the maize NAM population overlapped in position with significant genes in this study (Buckler et al., Science, 325:714-718, 2009), and with the population size and LD of this 503 diversity panel, we were able to obtain greater genic resolution at this QTL.

Two MADS-box transcription factors, zagl1 on chromosome 1 and zmm22 on chromosome 3, were identified as significant for controlling flowering time. MADS-box genes are particularly interesting candidates for flowering time due to their involvement in floral organ identity and patterning. GRMZM2G171650 (zmm22) encodes a StMADS-11 like transcription factor and this Glade of proteins act as a repressor of flowering in several species including wheat and rice. In addition, MADS-box genes have been shown to be frequent targets of selection during domestication and cultivar improvement. The MADS-box gene identified on chromosome 1 (GRMZM2G026223 [zagl1]) was previously shown to have a reduction of genetic variation in maize landraces compared to teosinte, providing evidence of selection during domestication. GRMZM2G171650 (zmm22) on chromosome 3 was previously shown to have genetic variation in both teosinte and maize landraces, but decreased genetic variation in cultivated inbreds, demonstrating evidence of improvement selection on this gene. Additionally, zmm22 was used as a marker in a QTL study involving a maize-teosinte backcross population for the mapping of domestication loci. Interestingly, zmm22 was within a 1-LOD confidence interval for eight of the 22 phenotypic traits that were mapped using data from one location. Traits included number of barren nodes, glume score, length of the primary lateral inflorescence, plant height, days to pollen, and the fraction of the primary lateral inflorescence internodes that are male (STAM). At a second location, the length of central spike, plant height, days to pollen, STAM, tassel branch number, and tassel branch space showed overlapping QTL on the same region of chromosome 3.

Example 2

Relationship Between Gene Expression (FPKM) of GRMZM2G171650 and Flowering Time.

Plant Materials and Nucleotide Isolation

A set of 503 diverse maize inbred lines was evaluated in this study, including 465 lines from the previously described Wisconsin Diversity Set (Hansey et al., Crop Science, 51:704-715, 2010). Plants were grown under greenhouse conditions (27° C./24° C. day/night and 16 h light/8 h dark) with six plants per pot (30 cm top diameter, 28 cm height, 14.5 L volume) in Metro-Mix 300 (Sun Gro Horticulture) with no additional fertilizer. Whole seedling tissue including roots at the V1 stage (Abendroth et al., PMR 1009, Iowa State University Extension, Ames Iowa, 2011) from three plants per inbred line was pooled. RNA was isolated using TRIZOL (Invitrogen) and purified with the RNeasy MinElute Cleanup kit (Qiagen). For obtaining DNA, seedling leaf tissue from five to 10 plants was bulked and DNA was extracted using the cetyl(trimethyl)ammonium bromide (CTAB) method (Saghai-Maroof et al., PNAS, 81:8014-8018, 1984).

RNAseq Library Construction and Sequencing

Individual RNAseq libraries were prepared for each of the 503 genotypes and sequenced on the Illumina HiSeq using standard protocols. Sequences are available in the Sequence Read Archive at the National Center for Biotechnology Information (BioProject accession number PRJNA189400). Transcript Abundance Profile Analysis in the Maize Pan Genome Sequence reads for each library were mapped to AGPv2 using Bowtie version 0.12.7 (Langmead et al., *Genome Biology*, 10 R25, 2009) and TopHat version 1.4.1 (Trapnell et al., *Bioinformatics*, 25:1105-1111, 2009) and normalized gene expression levels determined using Cufflinks version 1.3.0 (Trapnell et al., *Bioinformatics*, 28:511-515, 2010) with the parameters described in the Supplementary Text for RNAseq and Sample Quality Control Analysis. A gene/RTA was then defined as expressed if the fragments per kilobase of exon model per million fragments mapped (FPKM) low confidence interval as described by Cufflinks was greater than zero.

Figure 2:
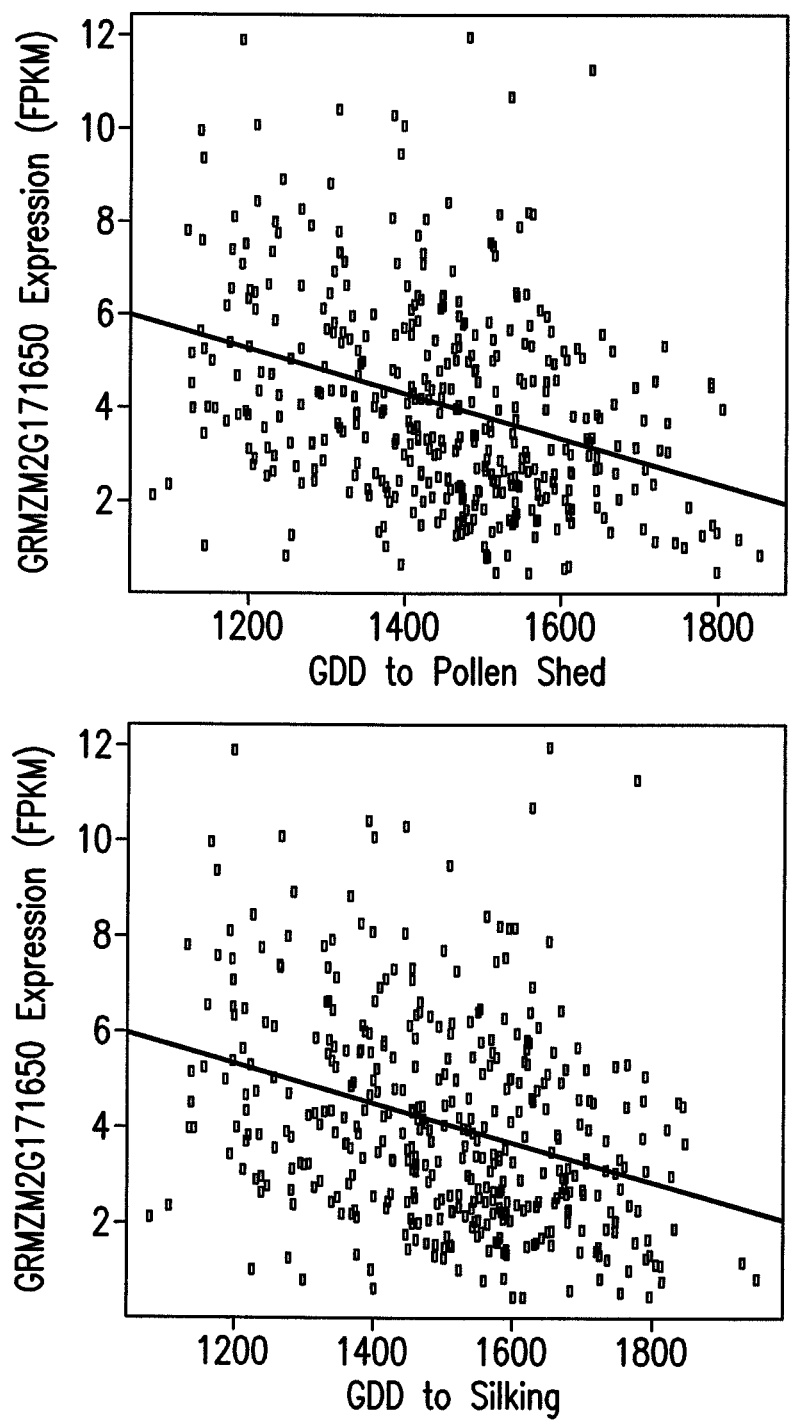
FIG. 2: Relationship between gene expression (FPKM) of GRMZM2G171650 and flowering time. Scatter plot of gene expression versus growing degree days (GDD) to (A) pollen shed, and (B) silking.

GDD to silk, and GDD to pollen shed were measured on plants grown in a randomized complete block design (RCBD) with two replications across two years at the Arlington Agriculture Research Station in Wisconsin. FIG. 2 shows a scatter plot of gene expression in FPKM versus growing degree days (GDD) to (A) pollen shed, and (B) silking. The figure shows an increase in gene expression at the seedling stage is correlated with earlier timing of expression. In other words, expression of GRMZM2G171650 promotes flowering.

What is claimed is:

1. A maize plant comprising a modification that suppresses expression of the gene of SEQ ID NO:1, wherein the plant exhibits delayed flowering time as a result of said modification relative to an otherwise isogenic plant lacking the modification, wherein the modification comprises a mutation in said gene of SEQ ID NO:1 or a recombinant construct comprising all or a portion of the sequence of SEQ ID NO:1, SEQ ID NO:6 and the reverse complement thereof, and wherein the transcription of the construct suppresses the expression of said gene.

2. A seed of the maize plant of claim 1, wherein the seed comprises said modification.

3. A cell of the maize plant of claim 1, wherein the cell comprises said modification.

4. A method of producing a plant commodity product comprising:
   (a) obtaining a plant according to claim 1; and
   (b) preparing the commodity product from said plant.

5. The method of claim 4, wherein the commodity product is grain, starch, seed oil, corn syrup, silage, meal, or protein.

* * * * *

SEQUENCE LISTING

```
<160> NUMBER OF SEQ ID NOS: 20

<210> SEQ ID NO 1
<211> LENGTH: 27945
<212> TYPE: DNA
<213> ORGANISM: Zea mays

<400> SEQUENCE: 1
gcagagcgac gagcgacgag ctaaacccg accgagtcgc tgcttgggtg cccaagatag      60
ccctaccgcc tcgcctctct cgttccccct catcgccacg ccagtcgcct ccactcccag     120
tcatctccca tcaccgacga cgtgtcgagg cgagagaaga gggcgagtcc aagtctaggg     180
ttcccgccgc atcgacacgg gcatcgcacc gcaccgcgag gggcgggcac ggaggaagat     240
ggcaccgcgc gggcgcgtgg agctgcggcg gatcgaggac aaggcgagcc ggcaggtgcg     300
cttctccaag cgccgcgcgg ggctgttcaa gaaggccttc gagctggccc tgctctgcga     360
cgccgaggtc gcgctcctcg tcttttcccc cggcggcaag ctctatgagt actcctcctc     420
caggttccgt acccctaccc catcgtcgta gaatcgcttg ccctgttga tcgaagtgag     480 attgaagcag gggaatagcc ccacccaaca atctagcggt ggagcagctg aggtgatcct     540
cgattcgctc cggcaccatt tggaccccc tcactcccgt tgctccatgg cctctcgcac     600
gcgcggtgga ccaccagccg ccttgatcgt gcacgccttg tgctcgagac aatcccccgt     660
atcaggactt caggaggctt cgtctgtgcc accttgcatg agtactatga ccctgtttag     720
tttgggatct ctatccgccc tgccgcttat agatggccaa acgggcggca cggcccgacc     780
cggcacgagc ccgacttggg cacggcacga caggcccgag cacgacaggc ccgtttacat     840
aatcgggccg tgccgtgccg cccgacgtgc ccagcctcag gcccaagcac ggcacgggag     900
attgttaacc gtgccgtgcc ggcccgacag cccgaagcac gttagggctc gtgccggccc     960
aagagcccgt aaaactcagt acagaaacgc aggaacatct aatacatata tttctcatca    1020
gatcagagtt aataacatat taatacaaca aaatctaaca caatcacaac acataacaca    1080
ttatttagtt tgagctggtg caatggctgc ctcgttaaaa acctatctag gtaaaactca    1140
cacctcgtga gaaaccctag ataggaaaag agtacagccc agctcaatat tttcattatt    1200
tcatcacata gttcatctca gaattaagtt acatgtccag aacccacatt acatgtccag    1260
aataccagaa cagactaatc aatgaataaa tctctgaagg actcttcaag gatcttatct    1320
tctgttgtgt gctgcattct tgcatctgct gcctcccaat cctttagcaa ggaaagcatc    1380
tccaccattc cagagccaag tcgacgacgc cgctcctcaa tgagcctacc tgcaagacta    1440
aatgctgatt ctgaactcac agtagagaca ggaactgaaa tgatatcttt agctaggatt    1500
```

```
gaaagtactg ggtaagtaag tttgtgatca tgccaccaat ctaggagatt gaattcatca   1560
tcaaacttct gaacagtgtc actatctaga taagcagcta gttcagaacc agaaatacca   1620
ggagtgcttg ctgcatgaag caaagcacta gcagatgtcc ttcttgacag ttcaggaacc   1680
atcccagaac tgctactggc accaaaggca cccagaccag cacccagtgc cattgaagaa   1740
ctgctaccaa tgccatctgc accaaacacc aaatcccaag catatttgct cttaccttca   1800
ccaggggtag catttgaagt cctctgcaac ctaacagaac caaatttgtc atcatattta   1860
ttaaataaat cagataaatc agccctcaca gaagttagat atccagagta atcagaatga   1920
gtcaactgag acatgagtgc aagcacattg ttgaaacctc tcattttagc tctagggtcc   1980
agtataaatg caaatgcata tagcaaagga attgtacccc aatattttaa gaatttgtct   2040
ttcattggga caactatatg tctaagcaaa ttatcattct catacatgtt catgtgctta   2100
ttaatatgaa gaatgtggtg caacattaaa ggtgatgtag gatagtacac accagacatc   2160
acaacagtag aatcataaaa cctttcaagg aactctaata ttttttcagc aacataccaa   2220
tgtgcttcac ttaaaagtgt agtaccctct tctctagggt gatagtgggt ctgtataaac   2280
acagagaatg tgctcttgta aggtataaga tgtttgagca taaggtaggt agagttccat   2340
ctcacttcca tatctaaacc aaacttacga ggtcttactc ccatagcaac acaaaaactt   2400
ttgtatgcag caatcctttg gtttgatgag ttcaaaaaag agatggcagt tctaaaatct   2460
tcaagataag gtttcagttc cacaaatgtg gcatgcacag caaggttaat gatatggcat   2520
gcacatcgtt gatgcaataa taaggaccaa acataagcag atagcaaagg tgtaagatgg   2580
tccattgccc tagtgttagc agatgcatta tccaaggtaa tggaaaaaac cttttcagcc   2640
aattcatatt cattaacaac agcatgaatc ctctctgcaa tgttcttgcc agagtgggaa   2700
caatcaatga gacgcatagc aagaatcctt ttttctaact gccaatcaga gttaacataa   2760
tgtgcaacaa cagacaaata atcttcttta gcattgccac tccaaatatc agaagttaaa   2820
gcaacagaag aaacatactt caatttttca gcaactatag catgtcgttc tttaaagtac   2880
ttttccatat ctctagttgt agtttgtcta gaaacattgc aatgcctagg attatgggca   2940
gttttaatgt attcatcaaa tgcatcacaa tcagcaaagc ataatggaag gtccaaccta   3000
gcaatcaaac gacataactg aacacgtgca acttcagcac tatattccca acgaaagaca   3060
gtaccatcag cattatatct tagcatagat tggttcccag ttcggccatg gagtcgttta   3120
catttgtccc tatgccgaga caaatgacca gtgccaatgg tagaacgggc agcaagttat   3180
ttcttgcaaa aatgacacct tgctcctact ctaacctcaa caccattttc agtggcgaaa   3240
atcttatcca tgtcctccca gacatcggac gtgcatttcc tctttctacc agtgcttgcc   3300
gtagtggagg cagtagcatc tgggagagcc tcgccctcgg cagcgacatt gtcgtcgcca   3360
aggtttatgg tagggttagg ggtagggtta ggggtagggg cagtggaacc aaagagatcc   3420
tccaaaccat cgtgcacgtc atccacatcg tctggggttt gacccatcaa caccaaatca   3480
tgattaatgg aggtaggatc ataccctatgc tccatcgccg gcacctggtc cctcacggcc   3540
acgacctcga cctgcaaaga agcaaagaca taggggggatt aggggggtta gggttaaaga   3600
agcaaaaaca gagggggatt agggtttagc gagttcatac cttagccgat taggccggag   3660
caccagttcc gtcggcgata gagaagatcc agcgacagca gatccagaga cacagagata   3720
gagccagata gaagaacaga gagactatga gcacaagcgc acgatataga tggccaaaca   3780
gggagaggag gtgtgtgtga agctttacct taccagatcc gcagaccatc ggtgatggat   3840
```

```
aagacagagg agaggcagat ccacagatct agtacaccgg agtccatagc agagggggga    3900
agcgctaggg aatggggata caagattctg ttaccgaaga cgtgccgagg acggggcatc    3960
caggattcca ggaagcacgg cgcgcgacgg ccgacgcctc gacgtcgacg gaactggcca    4020
ctgggtgcga ggcggcggtc gacggggaac cgagggaacc gggtgcgagc accgcgaggg    4080
aaccgatggc cggcgagccg agcaccacga gggaaccgac gaccggcgag tcgagcaccc    4140
acgagggaac cgacggcgg cgaggcgagc acccacgagg gaaccgacgg ggcgaaaagg     4200
cgactgggcg agggcggagc ggacagcgga gacggagaga acgagacgag tgcacgactg    4260
gggttagggt tagggttacg gacttcgggt cgtagaaagt aggaataggt agtcgggcct    4320
ggcgtgcttt ccgttttaaa cgggccgtgc cgggccggca cggcgtgcct tggtcgcggc    4380
ccaagcccgg cacgggcgta gtgccggcc ggcactagcc cgaatccgat cgtgccgtgc     4440
cgggctcagg cacgccaaat cgtgccgggc ctcgggccgg cccgactaac ccggcccatc    4500
tggccatctc tactgccgct gccgcccgca gcgccacctg ttctttatta ttattattat    4560
tgacgatccg tcacctgctc catgagcttg ttctggacct tggctgctcc aatgcgtgga    4620
gatagtgtgc gtgtgttctt tctctctttt tcacacgtgg ctcacagata ggaactcggg    4680
agcgtgcttc aatgccactg tgcgcgagta tctctcgtgc gggcaatgac aaatagggtg    4740
cacaccctcc aatttgcacc cggttacgtt gactcgactt ttcccgcact tctctcgtct    4800
aatctggagt caagtgagac ctgttcctgt gttctgattt ttttccgtct attgataacc    4860
ttggatcggc atccatcttg acttttttag aggagcctcc agctctactc tagaccaata    4920
atgttaaatg aatgtggcca agtccttcta tttagaaatt ttccaaaaaa attatagatt    4980
cttctcaaga cgaaagccat ttttatctcg tttgctagga cttttggta acctagaagt     5040
cctaccaagg acccttactc tgtaacatcc acgtggttga tatgcgtgat aggttaatta    5100
tagcaccgat taaggaagt gaacatatac agtggagatc tttagacaca ctagtgtgta     5160
atatagtgtg taataggatc ttaaagcggg atagcaacga aacgaaagat agaaaacggc    5220
taaagttgac atagaaagat gcattaaaaa gtgatttgaa aagacagaag agagttatcg    5280
agcatcgtct gagagacata acaagagaaa taacttagat atctatgaac caatttggtt    5340
tcatacttga aaggtcaact atgaaagcca tttccttaat aagttatgga gtagtatagc    5400
gagcaagcga aagacccaca catagatttc atcgactcga agaaggctta taacaaaatg    5460
ttaaaaaata ttatatggtg gtatggagaa acataacaaa atacgttaga ttcattaagg    5520
acatgtacaa caatgtttatg aatagtgttg aacaagttat aaggatgtat ataacttttt   5580
gattaaaata ggactatatc aagggtcaac tttgagcctt tacctttctg ccctagtgat    5640
agatgatgtc acaagggaat acatgagatg aacatgaata tatgagatat gtggctatac    5700
aagaatggat cgagttcaaa atgatgatat aggcaataga ttataagtag cactagcacc    5760
aattaaagaa aaacatattc aacatcgatt gagatagttt ggacatgtcc aacgagatc     5820
ccaaacacac tagtgtgtag tggaatccta aggcgtgaag cgtgatagta atgataaaag    5880
atgcgagaga atgccgaagc tgacataaaa agatgcagta aaagagactt gtgatgtagc    5940
ggtataaggg agaagaacct acacatggtt tttgacttag agaagactta tgacaaaaca    6000
taaaaaatgt tataggggg tttagacaaa taaaagtttc aatgaagttt gttaaggaca     6060
tgtacaacaa gtgtttcaac aagtgatgga gacatggctt tctaattaga ataggactgc    6120
atcaaggttc aactttgagg ccttaccttc ttgcctttat aatggatgag gatggatgag    6180
gtcacaaagg acatttaaag aggtatttct tagtgtatgt tttttgcgaa caatgtagtg    6240
```

```
ctagttgata aaagccggat aagagcaaat agaaaactaa agttgtggta ggagactata    6300
gagcccaaag gtttgacttg gtagaactaa accgaatac atgagatgtg agtatgtgac     6360
tttgacacta ctacacgtga gggagatatt agtttggaag gtcaagtagt gaccaggaag    6420
aatagatttt gatatttagg atcaattcta tagagaaatg ggatatagat atttaggatc    6480
aatactatag agaaatggaa tattgttagc catataatca aaagaagggc aaagaaagtg    6540
gcgctaaaca tctaccttat gcgtgataag agggtactac ataagctaaa agacaaatta    6600
gacatgtttt attatatgat gcataatatt ggtctacaaa agataagtt caacagataa     6660 gcattgcaaa aatatatatg ttatatacta gaattgtggc cacacgaggg atcaaatcga    6720
tgctatatat atgtgatagg ttagatatca gaatgaattc ataaaaaatg ataactaggg    6780
cgtagcatat cataaaagag aatgaattag cctacttaaa tcaagctttc ataggccatg    6840
ctactcttta ctcgactgtt caaggaaatc aaatcaagta gtgctagcag tcatgcaaat    6900
aaatcgttca tccttctctc tcatggttca tatgtcaggg cccaagaggg cccgctacag    6960
tgacactata gcgacgtggt actgtagcac gcccttaggt tggttagata aagataagac    7020
tagtttggga taagagatta gatctagtgc ttacaggtca agtaaccctc tttatataag    7080
gacagagatt gtatcaattg aaggtaacca agagattaga aggaaatctc ttctctcttg    7140
ccgaccgtgg gaaatagtg cgggtactgt ttatccatgt gaatagtacc gtgcctcccc     7200
agccaactgc ccgacgacgt ccaagcgtcg gtgtcttggt cctagacccc aaacctacca    7260
ctcgtactac ttcgtaaccc tagatccata acaatctagt atcagagacg acgtcgaccc    7320
tcaccctgga agtcgtagcc caagcggttg tcgatctcga ccgttccgtg gcgatcatca    7380
ccgccttcct ctccaccaat ttttcaccgc tagggcacac gtcccacacc aaccttttgc    7440
cgccgctgca tgcattgcca ggctcgatcc gtcaacctag caccccggcg gcaccatgcc    7500
tgcccattca tttgttgccc atgccgccgt cgccttcccc tattccatca tacgccatgg    7560
ctatggggga ccccagtaca ccatgccctt gccgcaaaca cagattgcga catcaggtgc    7620
aatcatccct tagggaggct tgcccctta cctcatctcc atgccaccat catcatcgcc    7680
aattccatcg tacaccctct catcatcaat ggcaccataa ttcacgatgg caacgtctcc    7740
ttcatcgacc ccgttgttca ccgccccatt cctgtgccgc cacagcagca gtgcgatgac    7800
gtcttctacg gggcgtggat ggcatccgag catcgatgac acaactatag gcggcggcat    7860
gctgcctcct agtgcgtcgg caaggacatc gccccatctt caagcggcgg cgctcagtcg    7920
tcccatcaac tagaggaagg cgattgcgtg ggcgagtgcc tgtaaggtgt cagcggtggt    7980
gcggctgcag tctgcctcct aatgcgctgg cgactgcagg aggtgcgtcg acagatgcat    8040
aacatcataa caccccgttt acctagccaa catttagatc cgactctaac caaacttttt    8100
tggttcaccc caacactacc cacttgtttg attgttgcta agcactttta ggataccaaa    8160
catacctccc aaatggtact aaagtggtc aatttaccat tgagtcaatg atatacatga     8220
taaattagag gtggcaccaa ttggaaaaaa agattgtccg acaataattg agatggtttg    8280
aacatatgtc caacggagac caatagatgc atcagtgcat agttgaactg gttagatgta    8340
taagtggatt gtcaccattc agtgcatagt tgaacggagt caatgtataa gtggattgtc    8400
tactctccta aaggcttaag cttttttggtt gaactggtta gaacgtccac tttaacatga    8460
taccgaagcc agacgtctcg agttcgaatc ctgacagagg ttgcccctgc ccctttattt    8520
ggttagaacg tccactttaa catgataccg aagccagacg tctcgagttt gaatctgtca    8580
```

```
ataccgaagc cagacgtctc gagtttgaat cctgacagag gttgcccctg ccccttttatt    8640
ttccacgttt gtgtctttcc tctcccgcta cacatgagtg agaatattaa agtgtataag    8700
tggattgact accttctctt aaaggcttaa gcttttaggt taaactagtt agagcgtcca    8760
ctctaacaac ttaacctaat acaaaatagt tctattaaaa ttaacgacat tacataagat    8820
gaactaaatc tatcatattg attcacatgg tacaaagaga gtaaggttta atgtcataat    8880
gtcacaacat acaattttcc atgagttctc gtgactacat cggtgtaggg taccttcaac    8940
ctcctctgcc tgtgccatat aggtaaaaag aatttgatta gaggtaaaaa ggataccgac    9000
taatcatgtg atggatgaag aaaatattcc atatctactg tacctcgtta acaggtacct    9060
atctctagtt atggttagtg cataccgttt gatataactg tgtttattaa caccatactc    9120
aatgaaataa tgtgttctct tttgctagac gaagattttt tttcaaaggt cacaatttac    9180
ggtgcagaca catgcatgat ttagtgtggg gcaaaaaggc atgatgtagt gatgaactca    9240
aaaggatggt ttaaattctt tttacatttg gaatttgagt ataggaaccg ttgtaccgta    9300
aagaaaatac aatacacaag tttaagtgtg taaccaagtc ctcaactcca ctccacaaaa    9360
acttacgtgg ccctgcagca cgttctgcgg tactatcaca acttagcgat cattggaaag    9420
ctgagggtat ttatacccac tcttctcaac ggccatctcg tgttttcat tctcaccatc    9480
cttaagataa ctcttctcac tccattgaag actcataagc tctacattga cttccttta    9540
gattcctttg agattagagt ctctaaactt tgttagagag ttattcaaac tgagatcaaa    9600
ctcttaaaac catggttatt aaagaggtaa aacgttaaaa cgttatgaac caacttttca    9660
acatttaaac gtttaaacga acgttgaaac atctttttaa acttgacata gaatttcaaa    9720
tatagaataa gttcatacat aagttgagtt cacaaaccaa ataacattag cataaaaaga    9780
aatagatcaa gttcaacaac acaagttcaa caaacacaag ttacaacttt tatgcatgat    9840
tattaaccat catcaaactt atcaatatta agaccatgag catcccatga taaattgaaa    9900
tcaactccaa gagcattgct aacatgagaa gaattagcta atggatcaac ccattcattg    9960
tcccaatcaa agtcttctaa aatcaaagga tcaaagtttt ttccttcctt acgtatttt    10020
taaaatctat caaccatctt tctgttgtat gaaagataga ccaaatcatt caaccttttg    10080
tgctctaacc tattcctctt ttggtatgca tctacaagta caaataaaag taaccaaaga    10140
agaactgagg ataaaaaagt agtggcgaat agaaattgaa taatttgact agctcattta    10200
caaatttaaa tgtactccaa ttccgctcac aaccggatga tgaagcacaa agactaacaa    10260
tccgtcttgc aaacttatat aattcaatag tacgaccacc atatgcaagc caccaatcaa    10320
ctaaaatggc gcgaacaaga agattatatg ttacatactg aaaatggagg aaggctatca    10380
attttagaat acttacgtgg attccttgtt tgtgcttctt cctctcatct gtctttgaca    10440
accctagcaa gtaaaggctc acgtagctca tgtaaagtag gaggcttgaa cccagatcca    10500
tattgagcaa tagcctccac aactacctca aattaccttg agttcgcagc attgaatggt    10560
ataccacact catagaaaaa cttggctatc tccaaacaaa tagaatttct ttcttcctta    10620
ggcttcatgg tagcacttat ggtagtttga gcaggtccct ttgcatgtct ctatgctaca    10680
acctcttgag gtgttcgtcg aatcatagat gcaatggact tctttggagc tgcaattggg    10740
tggggcttca attggaaaat tgctttgttt cttttggcag ctgctccaga acttggcaca    10800
atacatgagg aagcctgatg atgctgacac gacctgcttc ccataacttg gacatcatca    10860
tcttgtactg cttcatcttc cattcacacg tcatctaggt acaccgtcct agcccgcttc    10920
ccattattca aagcttcatt catctcttta tcaatctctc tagcagtgtt aggacacttg    10980
```

```
acaatgtctc catagccacc aggtagatgt ttcaccctct tgatacctcc ttttatttgt   11040
ttggggcaca aagcacattg aatcagctct cgctttcccg cctcaacata gtatgcatat   11100
ttctatcctg gatcatttga cttttggcctt agtcactgat ctttgagtgg gtcataggag   11160
tcattacttt gaccgacaga caatgcctcg ctatttgttg ccattgaaat tcactgtgag   11220
caaatagaga ttgattcact gtgagcaaaa tcaacaaatt cactttgagg ctggctgctg   11280
gtctggcgga gtggctgctc agctgctggt cttgctcagc agaggtgagg cagagcagcg   11340
caagtgacag gtgaggcttg cgcactggtg agagcaccta gagggggggg ggggtgaat   11400 aggtgatcct gtaaaaactt aaacttatag ccacaaaact tgattaggtg ttagcacagt   11460
ttatgccaag tggctagaga ggagtcaaaa cacaataacc acaagaatcc aatcacagag   11520
atgacacagt ggttatcccg tggttcggcc aagtacaaaa cttgcctact ccacgttgtg   11580
gcgtcccaac ggacgagagt tgcactcaac tcctctcaag tgatccaatg atcaacttga   11640
ataccacggt gttcttgctt ttcttttttct caatcccgtt tgcgaggaat ctccacaact   11700
tggagcctct cgccccttac aaaagatgtt cacagagaat cacagagcaa aggagggatt   11760
agcaactcac acacgacaca aagatcacag cgaatacgca cacacaagac ccagacttga   11820
gctcaaaaga ctagcacact agaacggagc tcaaatcact agaatgtcga caagtgcgc   11880 gagattgatg tgtgagtgat caagagtgct caaggaatgc ttggtgttct cctccatgcg   11940
ccaaggggtc cctttttatag ccccaaggca gctaggagcc gttgggaaca aatctggaag   12000
gccatctttg ccttctgtct cgtggcgcac cggacagtcc ggtgcacacc ggacactgtc   12060
cggtgcccga tttgttttcca tagaaagcga agccgaccgt tgccgaccgt tgcagatctg   12120
gcgcaccgga cagtccggtg cacaccggac agtccggtgc acaccggaca gtccggtgct   12180
cccttccgac cgttggctcg gccacgtgtc gcgcgccgat cgcgcggccg accgttggcc   12240
cggccgaccg ttggctcacc ggacagtccg gtgcacaccg gacagtccgg tgaattttag   12300
ccgaagtcgc cggagaaaaa acccgagaag cggctggttt gcgctgcgct gatctggcgc   12360
accagacact gtccggtgca caccggacag tccggtgccc cagcccgaag cagcctttgg   12420
ctgtacacag ccactctcca cttctttct tttcttcttt ctcctgtttc taacacttag   12480
acaagatgtt agtacacaaa actaatgtac taaggcttag aaacatacct ttacttgtga   12540
tttacacttt gttcatccat gagcatattt tcacatttag gcccttgtgt ttgcactcaa   12600
tcaccaaaat acttagaaat ggcccaaggg cacatttccc tttcaatctc cccctttttg   12660
gtgatttatg ccaacacaat ataaagcaac tagaacaagt gcaaaatcac tttaaaaact   12720
caaattggtt ttattcaatt ttggcatata tggatcatcc tttgccacca cttggttttgt   12780 ttttgcaaat caaactcaaa tctctatctc taagtcaaac acacatgttg aagtataaag   12840
agagtcattc caaaagagat tgatcaaaga tttcaaaaac tccccctttt tcccataatc   12900
aacacttctc cccacaagaa gccaactttt gaaaatagag acaataagag acaataaaag   12960
cttttgacaa acaaaaact ctattctact attttcaaaa tctctcaagt ggtagctgat   13020
ccatttatca ctttggcctt tattttctcc ccctttggca tcaagcacca aaacgggatc   13080
aatcttggcc cgttaacccc attgcctcac caaagtcttc aattaagagc aaatggcaat   13140
aagatttcat gagatgaact tggaattagt taccctctca tcggagtgca gtggaagtct   13200
ttcatggtcc aagtccacct tttcccttc aatcctcctt cgagactaaa ttatcaaact   13260
caagcacatg gttagtctca aagggtcaag ttgtaacaca tctcccccta cacatgtgca   13320
```

```
tcactttgca acggacttgt gaggtccagg gagtgtttgt acaacttgag caccataata    13380
agcaacataa tgcaaaaagg aacatgatca aaagcataac tacatgtatg ctacaattca    13440
atccaggttc cgcgaatcta agacatttag ctcactacgc aacctgcaaa aggtcttctc    13500
atctagaggc ttagtgaaga tatcggctag ctggttctcg gtgctaacat gaaacacttc    13560
gatatctccc ttttgctggt ggtctctcaa aaaagtgatg ccggatgtct atgtgctttg    13620
tgcggctgtg ttcaacagga ttttccgcca tgcggatagc actctcatta tcacatagga    13680
gtgggacttt gctcagattg tagccaaagt ccctgagggt ttgcctcatc caaagtagtt    13740
gcgcgcaaca ctgtcctgcg gcaacatact cggcctcagc ggtggatagg gcaacggaag    13800
tttgtttctt agagttccat gacaccaggg accttcctaa gaattggcac gtccccgatg    13860
tactcttcct atcgacctta catccagcat agtcggagtc tgagtatcca actaagtcaa    13920
aggtagaccc ctttggatac cagagcccga agcaaggcgt agcaaccaaa tatctaagaa    13980
ttcgcttcac cgccactaag tgacactcct taggatcgga ttgaaatcta gcacacatgc    14040
atacgctaag cataatatcc ggtctactag cacataagta aagcaaagaa cctatcattg    14100
accggtatgc ttttgatca acggacttac ttcctttgtt gaggtcggtg tgtccgtcgg    14160
tccccatcgg agtctttgcg ggcttggcgt ccttcatccc aaaccgcttt agcagatctt    14220
gcgtgtactt cgtttgggag atgaaggtgc cgtccttgag ttgcttcact tggaacccaa    14280
ggaagtagtt caactcgccc atcatcgaca tctcgaattt ctgcgtcatc ccctgctaa     14340 actcttcaca agactttggg ttagtagaac caaatattat gtcatcgaca taaatttggc    14400
acacaaacaa atcaccatta caagtcttag taaaaagagt tggatcggct ttcccaacct    14460
tgaaagcatt agcaattaag aaatctctaa ggcattcata ccatgctctt ggggcttgct    14520
taagtccata gagcgcctta gagagcttac acacatggtc ggagtaccgt tcatcctcga    14580 agccagggggg ttgctccacg tacacctcct ccttgattgg cccgttgagg aaggcgctct    14640
tcacatccat ttgaaacaac ctgaaagaat ggtgagcggc atatgctagc aagatacgaa    14700
ttgattctag cctagccaca ggagcaaaag tctcctcgaa atccaaacct gcgacttggg    14760
cataaccttt tgccacaagt cgagccttgt tcctcgtcac caccccgtgc tgtcctgtt    14820 tgttgcggaa cacccacttg gttcccacaa cattttgctt cggacgaggc accagtgtcc    14880
aaacttcatt gcgcttgaag ttgtttaact cctcttgcat ggccaacacc cagtccggat    14940
ctagcaaggc ctcttctacc ctgaaaggct caatagaaga gacaaaggag taatgctcac    15000
aaaaattaac taatcgagat cgagtagtta ctcccttgct aatgtcaccc agaatttggt    15060
cgacgggatg atccctttga atcatcgctc gaacttgagt tggaggtgcc ggttgcgctt    15120
cttcctgtat cacttgatca tcttgtgctc ccccttgatc aagcgcctcc acttgaggta    15180
cctgttcgtc atctttggtt gggggttgca ccatagttga ggaagaagtt tgatctcgtt    15240
catcttgttc ctgtggccgt acttctccaa tcgccatggt ccgtatagcg gccgtcggaa    15300
catcttcttc atctacatca tcacaatcaa caacttgctc tcttggagag ccattagtct    15360
catcaaatac aacgtcgcta gagacttcaa ccaaacccga tgatttgttg aagactctat    15420
acgcctttgt atttgagtca taacctaata aaaacccttc tacagctttg ggagcaaact    15480
tagaatttct acccttcttt actagaatgt agcatttact cccaaataca cgaaagtacg    15540
atacattggg tttgttaccg gttagtagct catacgacgt cttcttgagg aggcgatgaa    15600
ggtagaccct gttgatggcg tggcacgccg tgttcacggc ttccgtccaa aagcactcgg    15660
gggtcttgaa ctctcctagc atcgtcctcg ccatgtcgat gagcgtcctg ttcttcctct    15720
```

```
ctaccacacc attttgctgt ggtgtgtagg gagcggagaa ctcgtgcttg atcccttcct    15780
cttcaaggaa ctcctccact tgaaggttct tgaactcgga cccgttgtcg cttcttatct    15840
ttttcacttt gagctcaaac tcattttgag ctctcctgag gaagcgtttg agggtccctt    15900
gggtttcaga cttatcctgc aaaaagaaca cccaagtgaa gcgggaaaaa tcatcaacaa    15960
taactaaacc atacttactt cccctatgc ttagataggc gacgggtccg aagaggtcca     16020
tatgcagcag ctccaggggt cttgaagtgg tcatcacatt cttgctgtga tgcgctcctc    16080
ccacctgttt ccctgcttga caagctgcac aaggtctatc tttttcgaat tgaacattgg    16140
ttagacctat cacgtgttct ccctttagaa gcttgtgaag gttcttcatc cccacatgtg    16200
ctaagcggcg atgccacagc cagcccatgc aagtcttagc cattaagcat gcatctagac    16260
cggcctcttc ttttgcaaaa tcaactaaat aaagtttgcc gtctaataca cccttaaaag    16320
ctagtgaacc atcacttctt ctaaagacag acacatctat atttgtaaac agacagttat    16380
atcccatatt gcacaattga ctaacagata gtaaattata tcctagtgac tctactaaaa    16440
acacattaga gatagagtgc tcattagaaa ttgcaatttt acctaacccct tttaccttgc    16500 cttgattccc atcaccgaat atgattgaat cttgggaatc cttattcttg acgtaggagg    16560
tgaacatctt cttctccccc gtcatatggt ttgtgcatcc gctatcaata atccagcttg    16620 aaccccgga tgcataaacc tgcaaggcaa atttaggctt gggtcttagg tacccaactc     16680
atgttgggtc ctacaaggtt agtgcaaata tccttaggga cccaaatgca gttttgtct    16740 cccttgcatt ttgcccctaa cttcctagca acaattttct tatcctttct acaaatagca    16800
aaggaagcat ttaaagcata ataaattgtg gaaggttcat ttgctatttt cctaggagca    16860
tgaataacat tccttctagg cacatgatga atagcatttc ttttaggaac aacatttctc    16920
ctagtaacat ttctatcata cacataagag gaactaggag caaacatggt atgagaatca    16980
taaacatatg aatcataagc atcatgactt acatttctag tttgtcttct atcatgatac    17040
aaaaatgcat ggttcctttt agcactagta gccatagggg ccttcccttt ctccttggcg    17100
ggaatgggag cctatggct tgttaagttc ttagcttctc tcttgaagcc aagtccatcc     17160
ttaattgagg ggtgtctacc aattgtgtag gcatcccttg caaattttag cttatcgaaa    17220
tcattcttgc tagtcttaag ttgagcatta agactagcca gttcatcatt aagcttggaa    17280
attgaaacta ggtgttcact acaagcatta atgtcaaagt cttacacct agtacaaatt     17340 tcaacatgtt ctacacaaga attggatttg tttgctactt ctaatttagc atttaaatca    17400
ttgttgacac ctttcaaagt agaaatggtt tcatgacaag tagatagttc aaaagaaagc    17460
atttcatttc tcttaacttc taaagcatag gattttgtgt cctcaacaaa tttatcatgc    17520
tcttcataca acaaatcctc ttgcttttct aaaagtatat tcttttcatt caaggcatca    17580
attaattcat taattttgtc tatcttagat ctatctaagc ccttgaacaa acatgaataa    17640
tctacttcat cctcatcact agattcgtcc tcacttgaag aagcataggt agagttgcga    17700
gtacatacct tcttctctct tgccataagg catgtgtgac gctcgttggg gaagagggtt    17760
gatttgttga aggcggtggc ggcgagtcct tcattgtcgg agtcggacga ggagcaatcc    17820
gagtcccact ccttgcctag atgcgcctcg cccttttgcct tcttgtaatg cttcttcttt    17880
tccctcttgt tcccctttc ctggtcacta tcattatcag gacagttagc aataaaatga     17940
ccaagcttac cgcatttgaa gcatgatcgc ttccccttgg tcttagtctt gctcggctgt    18000
ccattgcgac cctttagcac cgtcttgaat ctcttgataa tgagggccat ttcttcttca    18060
```

```
ttaagaccgg ccgcctcaat ttgcgccacc ttgctgggta gcgcctcctt gttccctgtg   18120
gctttgagag caaaaggttg cggctcgttg atcggtccat tcaaggcgtc gtccacatac   18180
cttgcctcct tgatcatcat tcgcccgctg acgaattttc ctagtacttc ttcgggcgac   18240
attttggtgt acctgggatt ctcacgaata ttattcacca aatgaggatc aagaacggta   18300
aaggacctga gcattagtcg gacgacgtcg tggtccgtcc atcgcgtgct tccgtagctc   18360
cttattttgt tgacaagggt cttgagccgg ttgtatgttt gagttggctc ctcgcccctt   18420
atcatcgcga accgtccaag ctcgccctcc accaactcca ttttggtgag caaggtagcg   18480
tcatttccct catgagagat cttgagggta tcccagattt gcttggcgtt atccaagcca   18540
ctcactttat tatattcatc cctgcacaat gaggctagaa aacagtagt agcttgtgca   18600 ttcttatgga tttgctcatt aatgaatata ggactatccg aactattaaa gtgcattcca   18660
ctatctacaa tctcccatat gctaggatgg agagagaata ggtgactacg cattttgtgg   18720
ctccaaaatc cgtagtcctc cccatcaaag tgtggggggct tgccgagtgg aatggaaagc   18780
aaatgtgaat ttgaactatg cggaatacga gagtagtcaa aagaaaagtt agaattaacc   18840
ggtttccttt gtttgtcgta gtcgtcgtcc ttttgggaag aagaggactc atcgctgtcg   18900
tagtagacga tctccttgat gcgtcttgtc ttcttcttct tcccatctct tcgcttgtgg   18960
cccgagcccg agtcattgga cttgtcatcc cttggctcgt tgacgaagga ctccttctcc   19020
ttgtcgttga tcacaattcc cttcccctta ggatccatct cttcgggcgg ttagtccctt   19080
tcttgaagag aacggctccg ataccaattg agagcaccta gagggggggg ggggtgaata   19140
ggtgatcctg taaaaactta aacttatagc cacaaaactt gattaggtgt tagcacagtt   19200
tatgccaagt ggctagagag gagtcaaaac acaataacca caagaatcca atcacagaga   19260
tgacacagtg gttatcccgt ggttcggcca agtacaaaac ttgcctactc cacgttgtgg   19320
cgtcccaacg gacgagagtt gcactcaact cctctcaagt gatccaatga tcaacttgaa   19380
taccacggtg ttcttgcttt tcttttctca atcccgtttg cgaggaatct ccacaacttg   19440
gagcctctcg cccttacaaa agatgttcac agagaatcac agagcaaagg agggattagc   19500
aactcacaca cgacacaaag atcacagcga atacgcacac acaagaccca gacttgagct   19560
caaaagacta gcacactaga acggagctca aatcactaga atgtcgaaca agtgcgcgag   19620
attgatgtgt gagtgatcaa gagtgctcaa ggaatgcttg gtatgctcct ccatgcgcca   19680
aggggtccct tttatagccc caaggcagct aggagccgtt gggaacaaat ctggaaggcc   19740
atctttgcct tctgtctcgt ggcgcaccgg acagtccggt gcacaccgga cactgtccgg   19800
tgcccgattt gtttccatag aaagcgaagc cgaccgttgc cgaccgttgc agatctggcg   19860
caccggacag tccggtgcac accgacagt ccggtgctcc cttccgaccg ttggctcggc   19920
cacgtgtcgc gcgccgatcg cgcggccgac cgttggcccg gccgaccgtt ggctcaccgg   19980
acagtccggt gcacaccgga cagtccggtg aattttagcc gaagtcgccg gagaaaaacc   20040
cgagagcggc tggtttgcgc tgcgctgatc tggcgcaccg gacactgtcc ggtgcacacc   20100
ggacagtccg gtgccccagc ccgaagcagc cttggctgt acacagccac tctccacttc   20160
ttttcttttc ttctttctcc tgtttctaac acttagacaa gatgttagta cacaaaacta   20220
atgtactaag gcttagaaac ataccttac ttgtgattta cactttgttc atccatgagc   20280
atattttcac atttaggccc ttgtgtttgc actcaatcac caaatactt agaaatggcc   20340 caagggcaca tttcccttc aactggcggc ttgcgcagag cagcgcaacg aggcagaaca   20400
acgcagaggt gaggtagagc actggcggcg gcggcacact ggactttgga gcggcgccgc   20460
```

```
actgcactgt gggcggaggg aggagggagt agaggggccg acggcgtgcc tggactcctg    20520
gaggcggctg agggcggctg aggacaatcg acggcggtag caggctgagg acggctggcg    20580
gctgaggacg gctaaggatt tagggtttga gggcgactga ggacggctaa aggcctagga    20640
aggcccacta caaactagaa tgttcataga acgcttaaaa caccataaaa cacgttttag    20700
acggttacac gacgcttaaa cgtccaaaac ggacgttcaa caccattttc ttagaacatg    20760
cggacgtttt agttcctact cacgttttat cgcttaaaag acgcttaaac gtcgtttaag    20820
cgacgtttta ataacaatgc ttaaaacact tagttctcac tcaaaccggt ggattgcgac    20880
ctagatcaaa cttctagaac acttagttgt cactcaaatc ggtagattgc attcgttgct    20940
cttgaaaaag ggctcctagc cggctagaca tcttctattc actcaagccc ttgtgggtac    21000
tccaaaaagt ttgtaatctc tatcaacatc tagtaagaac tctcaatcaa gagacttgca    21060
ctcttaactt tagttctcac tcaagacggt agattgtatt cgttgctctt gaaaaaaagg    21120
ctcatagtcg gctaggcatc tcctattcac tcaagccctt tgggtactc caaaaaaaat     21180 tgtaatctct accaacatct aggaagagct ctcaatcaag agacttgtgc tcttaacttg    21240
agaagtgtac atagttcttg aaaccaagtc tggatggctt cctcaacatg gaggtgacaa    21300
tccttagtgg catgctaaac catagaataa atcatttgtc ccttgtgttt tttatgatcg    21360
tattatgttc tacttatgtt gtggttggtt tagggtttgc gcccgatcta cttgtactta    21420
agcttttgac atcgttgtga attagactca aagctaccac aagaaccttta gtaaatcact    21480 cgatctaagt tctcttagat agtttttgaa tttatacat gaggtacctc gggtgcggta    21540
gtaccacatc aatacccaaa actgtcgtgg cacggtgatc ctcacgcaag cacgagagta    21600
tcgcgtctga ttctaactgt tatattaagt ttgttttata tgtctattga accatggttc    21660
ttaaggcggt aagacgaggc aaggcgttgg accaccgcct ggacgcctag gcaacaccta    21720
gccgcttact aaggagagca aggggacacc ttaccaatta gagaaataga agaacaacat    21780
agatgaggaa gaaaaagcac cttaccaatt agagaaatag aagaacaaca tagatgagga    21840
agaaaaagga aaaggaaggg ctaggagatg tataagagat ggcctatccc atcagctagc    21900
ccatataacc ttccctgcta gtgattaggg ttaccccagt ctcacgatgc tgctcgccgg    21960
catctcagcg tcacctctcc tgctcccccg agctctacgc cgctgctccc ccagctttgt    22020
gccgttgttg cccctgagct gtacgccacc gctcgccctg agctctgcat tgtcggtcgc    22080
cgctctctcg agctctgtgc cgccactgtc ccaagctcta taccgtcgcc taggcttctt    22140 cccttcccc tcttacctcg cttgctgatt cttagctagg cggggacgcc tagaactttt     22200
gggcgcctgg acttaggtgt cacctaggcg acacctttga aaccatgtat tcaaaccct     22260 atagacttgc atgatccttt ttcactacca gaacccaaga tttggcaaag tcgccacatc    22320
cacttgctgc tgtgcatgtt gcatatcact aaaaaataag tgtggtaaat gctaaaataa    22380
atctagaaag aaaaagtag aaaaatacga gtacttattg atacaactta tgaatattca     22440
catattcgat atcgtttcta ccgcgatgtg tcgatcttct gtaactatgg taatatgaga    22500
agtttgtgaa tttaaataaa tgaaataaaa tgatacttaa cacatgtttt tatctttcta    22560
caatcaaatc ttggacttcc acaatgctcg tgaagaaccc tctatccctt ggaattattc    22620
ctcgtttgtg ccggattggt gggtcggaac gattcctaac cggattgctt ctctaattta    22680
tataaacttt aattagctga aacgattccg gatgcaatcc gatagaaacg aacaaggcct    22740
aaagtgattg tgatgccttg ttgctagcct agcggtcaac cattattgtc gcattgtaat    22800
```

```
tatcagatga caatgggtat gaatccattt tgtattgtcc atctatacct acaattgatg    22860
ggataaatgg gtatgaatcc attttgcatt gtccatctat acctacaatt gatgggataa    22920
atcgtaccca tcaaacttta cctgatctag gtacaaactc agatacatac ccatgctctg    22980
atgctcataa gaggttgaat tgctacgaca gcttgtccaa aggcagcaac aagtaccaca    23040
acctcatgat gtgtacaacc accaccagcc tctggttgtg agctaccagg atttcgattt    23100
cttgagtaca caactgttca acaagactga agaatccact ctgatgcttg gatatgcatg    23160
gagatgcttt cagtagtttg tttggatgaa agcaaggcca gatttggtgc tcaacaactg    23220
cgatgattgg ctcgtctatg tggaacaact atcacgtcat actctcagca gatcacattt    23280
tctcatagga agaatttaag ataactttct ggaaggacta acggagaggg tttctaggac    23340
tgacccaaga caactgcacc atactctagt atggtcaagc tttcgaaatc tatgccagta    23400
tgtaggatat catggagaca cggatgccaa aaaagagatc gttttcgtcg gcctcaatac    23460
catgctcaaa caacgcctaa acccggtgaa agtagacatg tacaataaaa ttatgaactt    23520
ggctatcacg caagaagact gcatcatgcc tcggagaagt gaaaggcccc aattgcacca    23580
tcaaatgccc agaatcagaa attcaagctc gtctccaatg cactggccag agtttctcaa    23640
gcatcacaac ccgaatgtta ggtaatacaa ccaccgcagc aacagggtaa cacccgtttt    23700
accgttccac cacccaagac acaaggccca ttttcagca gcagaatcgt cctggccaac    23760
ataggaatag gtgctttact tgaagtaaag gacactttca cttcagaatt ttgtttcttt    23820
ctttggtcca agttcgtttc aaggaattac tctaaaacgt caagatctca tatctattaa    23880
acaccatgat ctcacatcag acgtcatgac tcatctgttt ttccttactt tataggtagt    23940
ttgatgtgaa gttcaaagca ttgctcttta attgaatcaa agaatctctt gaaacaaaga    24000
gtaaggaaat ttcaaatttt attctaaaaa tttgaattta ttgcactttg ttttcatatg    24060
attttataac ctagacacga actcacttgt aaccttatct acatagaagt agacatttaa    24120
attgtgtcca atgaatcttc tatcgtagaa actaaatcca aggtatgttg tgacaagcta    24180
aaccgaggta tattagctta ggatctaatc ccacccattg ttcccaaaag gtggaggcaa    24240
atagtgctga tgccctgcta ccatgttttt ccttttcagc atagaagata catatgaccg    24300
ctatcatcaa tttgcgggag caggaagaaa agtgaacgga cataacaacg atgtaaagat    24360
ctcaataaga cttttagctg catcacttac agtccagttt tagattggga aggaaacaat    24420
tatcgattgt ggaattcctc aatatatgtc gcttcacttg ccattaattt gcccagtatt    24480
ttgttcgctt gcgttgtcct ttgtagtata attacccaaa cggagtggac acttcatcta    24540
cacacaaaag agacatcctg ttatttttct gttaattata gctgactaaa gagacattct    24600 gttattttc tgataaatac agctgactaa agtattttgc cccagaaccg ggatgtagct    24660
gcttcagatt tacagtcgag acttaaggag atcgcaacat ggtaacacta agttttcact    24720
actctctccc aactttctat gttcaatggt ggcaacaatg taacaaacct gcaggtctaa    24780
acaaaacaac gctgaggagt cggatgccaa tgaacttgag aaacttgagg aactcctgac    24840
aaatgctttg aggaatacga aagccaaaaa ggtacagtaa aatgcctttc ttttactacg    24900
tcatgtatcg ttgcggctga tgatttagat agagatctcg ctccaaaaac ttttgatac    24960 attttgtatt cctatcctgc ggaccaatta ttgctacaat actttggtgc atggttttct    25020
gatgttttct accttcccaa tttccacgca gacaagagaa ttatcatctg acaaagtaaa    25080
aatattcaaa acattgcgtg ttggtcagca ttgaacaatg atattagctg ctaggtgtca    25140
accagtcaac cagagagtat atggtgtcat attttcaaag acgtcgttaa taatatgaga    25200
```

```
caacagaagt ggcatcgtcc tagtactgct ctagtattat gtgaaagaag gatatccagt   25260
gaggtgagca acgtcccgac cccagccccc gcatcgtcct ccgctcgagc gacacaggtt   25320
gcccctaaac tctaaaccct agcgctgcca cccctccgc ctccctccac cccctcgcag    25380
tcgctggagg agtccgccgt aggccagcac gggcccaag gatggcggca cgaaaagttc    25440
ttctttcgat tggtctccct atgctttaga tttgaaaggg tttgctgtgc agcttagtcg   25500
cgacgcggcg gcaggtaggc gggcgtgtgc cgtggtggcg tctaggtgga caaggtccca   25560
cacgcgggcg tggcgttgtg tgtgcgggaa gcgtggctcg gccacgtctt ggcgctccgc   25620
aagctcagcc acggcctcca ggacggcttc agcgttggct tcctgctcca cgtcgccgtg   25680
ggcgagctcg tctcctcgca ttgccaaaac agggaagatg ctgtcgacca atgacgtgcg   25740
aagcttggag gccgagaggg gttagggcgg cggtggctgc ggtctggtcc tacgcggtg   25800 ctccgaggtt gggtggctcg acggcagccg agaacgtgtc agctcggggc gacggtgggc   25860
tagcaaagtg gccccagcgg cgccggctgt ggtgcgcgcg ccagcacctc agacccgcca   25920
cgtcacggct gttgctataa ggtttggcta ccgagggt gctgcaccag gcgactgctg     25980
gcaacgagtt gcgagacacg cccgacgact gctggcttag gtggccgcat tttccagggt   26040
cgacgacaac tgctagcaac gactccggcg cgtggtagtg tcgcacgtgg catggtggtg   26100
cccggttcca tctgcccaac tcgaggggtg gcagctgccg cggcaatcgg tgcgtcgatg   26160
cccatctgga aggtttgtgc gggtgtcggg gcaacgacga cgacggaggt agcttgcttt   26220
gaccttgact tgacgttgtg ttgggggact tcgtcaaggc tttcgacgcc gatgacgctc   26280
gtgagcgtcg cttacccact tgagagcgtc gcattcctca gcactgtctt ctatgggtga   26340
aagcctgtca tcttggacat gcgacgatga cgtctgcaac gtcactccct tcctgaagag   26400
gtcgctattg aagttttgtc ccgaccacga catcgctttt ctgtagatgc tttcgcttct   26460
tagcgtttgg tatgcgggtg gaggtacggt gttggagcgt aaagtcgaag ctgctacgtc   26520
aggggatgtg gctcgtcaat gatgacgtga gacgccccct tcttcgtgga aggattgctt   26580
ctgaggttag gcatatgttg ggaacgagcg ggaagatcaa gattgaaagt cccgttcgtg   26640
aagaatcgga gctgcctcac gtgtggtgtc tcgaggcttg acaatgacga cgctccgcgg   26700
tcttcctcca tttgtgttag tgtttggcta tagacgtcgt ccagttttct ttggtccatt   26760
atgttgagct cgacaacgat gactctggat gagttttatg tgtgaggctg ccattgcttg   26820
ggtagtttgt acaccttgcg taggttttgg gtccgatttt acttaaaact gtgtcaattc   26880
cattcttaat taagggacag ctaaaaaata ttatgtgaaa atctaacatc aatgccgga    26940 agccctgtca gagctcaact cagttatgta gctctactct taagtaggac aagataacaa   27000
acgccaaaag tcattcttgt tatattctaa ttgagctttt ttggtatgat ttcgacggca   27060
agtggatcgt gctgccttac tattctagag tcaaccattt gtaagctgga cacagtaaac   27120
gtgcatacga accatgtctc acaaaatgtt ctgtttgtat atcctgaagc ttgaaaggaa   27180
caccgttcat cagaatggaa ctcgtcagtc atctcagaaa aaaaagaga ttattgctca    27240 ctatgaatca tttttacga aattggtaaa tgcagctatg tattcctcgc atgttagtct    27300
gaagttctct attatgatga aatgcagatg ttggcaaaag aaaacaatgg tggtgccggt   27360
gcaagtacaa gcagccagat gttgctttac tcggcagagc gtgcaaccga caaatgaaac   27420
ggggcgtgca tctgttgcta acggggcggt gccggtgccg catactattg ttgtgtagct   27480
gaggtttgtc aaggtggctg ctggcaaggt tagccgagga agtggagttc aataacagga   27540
```

| | |
|---|---:|
| tgcggaaact gtgccgctcc ttgccgaact aagcccccgt tacgttgtcg cacaaagttt | 27600 |
| atttcctagc actgtgcttg ctgcttatgt ttgtttggat gtgccaacct gcagtgaccc | 27660 |
| tcgtggagcc tgggtctcac gctcctctta cctagtgtga tgtgcagaaa aagtgtgatg | 27720 |
| ctgtaaaatt atgtgattgc ctagcagatg tcaaattttc aatcagtagc taactccttt | 27780 |
| taatggtaca ggcttgcatg atttcatctg caaaaagag agggcgggtt gggtgtcaaa | 27840 |
| tctagccgga tgttttcgca agtttgtgat aaaaattgtg ctgtacactt gtgtttatgc | 27900 |
| agttgcccta ggcgtcagtg ggctgaaagg taatatctgt gaatt | 27945 |

<210> SEQ ID NO 2
<211> LENGTH: 716
<212> TYPE: DNA
<213> ORGANISM: Zea mays

<400> SEQUENCE: 2

| | |
|---|---:|
| gcagagcgac gagcgacgag ctaaaccccg accgagtcgc tgcttgggtg cccaagatag | 60 |
| ccctaccgcc tcgcctctct cgttccccct catcgccacg ccagtcgcct ccactcccag | 120 |
| tcatctccca tcaccgacga cgtgtcgagg cgagagaaga gggcgagtcc aagtctaggg | 180 |
| ttcccgccgc atcgacacgg gcatcgcacc gcaccgcgag gggcgggcac ggaggaagat | 240 |
| ggcaccgcgc gggcgcgtgg agctgcggcg gatcgaggac aaggcgagcc ggcaggtgcg | 300 |
| cttctccaag cgccgcgcgg ggctgttcaa gaaggccttc gagctggccc tgctctgcga | 360 |
| cgccgaggtc gcgctcctcg tcttttcccc cggcggcaag ctctatgagt actcctcctc | 420 |
| cagaaccggg atgtagctgc ttcagattta cagtcgagac ttaaggagat cgcaacatgg | 480 |
| tctaaacaaa acaacgctga ggagtcggat gccaatgaac ttgagaaact tgaggaactc | 540 |
| ctgacaaatg ctttgaggaa tacgaaagcc aaaaaggtac agtaaaatgc ctttctttta | 600 |
| ctacgtcatg tatcgttgcg gctgatgatt tagatagaga tctcgctcca aaaactttt | 660 |
| gatacatttt gtattcctat cctgcggacc aattattgct acaatacttt ggtgca | 716 |

<210> SEQ ID NO 3
<211> LENGTH: 799
<212> TYPE: DNA
<213> ORGANISM: Zea mays

<400> SEQUENCE: 3

| | |
|---|---:|
| gcagagcgac gagcgacgag ctaaaccccg accgagtcgc tgcttgggtg cccaagatag | 60 |
| ccctaccgcc tcgcctctct cgttccccct catcgccacg ccagtcgcct ccactcccag | 120 |
| tcatctccca tcaccgacga cgtgtcgagg cgagagaaga gggcgagtcc aagtctaggg | 180 |
| ttcccgccgc atcgacacgg gcatcgcacc gcaccgcgag gggcgggcac ggaggaagat | 240 |
| ggcaccgcgc gggcgcgtgg agctgcggcg gatcgaggac aaggcgagcc ggcaggtgcg | 300 |
| cttctccaag cgccgcgcgg ggctgttcaa gaaggccttc gagctggccc tgctctgcga | 360 |
| cgccgaggtc gcgctcctcg tcttttcccc cggcggcaag ctctatgagt actcctcctc | 420 |
| cagaaccggg atgtagctgc ttcagattta cagtcgagac ttaaggagat cgcaacatgg | 480 |
| taacactaag ttttcactac tctctcccaa ctttctatgt tcaatggtgg caacaatgta | 540 |
| acaaacctgc aggtctaaac aaaacaacgc tgaggagtcg gatgccaatg aacttgagaa | 600 |
| acttgaggaa ctcctgacaa atgctttgag gaatacgaaa gccaaaaaga tgttggcaaa | 660 |
| agaaaacaat ggtggtgccg gtgcaagtac aagcagccag atgttgcttt actcggcaga | 720 |
| gcgtgcaacc gacaaatgaa actgtgccgc tccttgccga acttaagccc cgttacgttg | 780 |

```
tcgcacaaag tttatttcc                                                799
```

<210> SEQ ID NO 4
<211> LENGTH: 1332
<212> TYPE: DNA
<213> ORGANISM: Zea mays

<400> SEQUENCE: 4

```
gcagagcgac gagcgacgag ctaaaccccg accgagtcgc tgcttgggtg cccaagatag      60
ccctaccgcc tcgcctctct cgttcccccct catcgccacg ccagtcgcct ccactcccag    120
tcatctccca tcaccgacga cgtgtcgagg cgagagaaga gggcgagtcc aagtctaggg    180
ttcccgccgc atcgacacgg gcatcgcacc gcaccgcgag gggcgggcac ggaggaagat    240
ggcaccgcgc gggcgcgtgg agctgcggcg gatcgaggac aaggcgagcc ggcaggtgcg    300
cttctccaag cgccgcgcgg ggctgttcaa gaaggccttc gagctggccc tgctctgcga    360
cgccgaggtc gcgctcctcg tcttttcccc cggcggcaag ctctatgagt actcctcctc    420
caggtagttt gatgtgaagt tcaaagcatt gctctttaat tgaatcaaag aatctcttga    480
aacaaagaca tagaagatac atatgaccgc tatcatcaat ttgcgggagc aggaagaaaa    540
gtgaacggac ataacaacga taaccgggat gtagctgctt cagatttaca gtcgagactt    600
aaggagatcg caacatggtc taaacaaaac aacgctgagg agtcggatgc caatgaactt    660
gagaaacttg aggaactcct gacaaatgct ttgaggaata cgaaagccaa aaagatgttg    720
gcaaaagaaa acaatggtgg tgccggtgca agtacaagca gccagatgtt gctttactcg    780
gcagagcgtg caaccgacaa atgaaacggg gcgtgcatct gttgctaacg gggcggtgcc    840
ggtgccgcat actattgttg tgtagctgag gtttgtcaag gtggctgctg caaggttag    900
ccgaggaagt ggagttcaat aacaggatgc ggaaactgtg ccgctccttg ccgaacttaa    960
gccccgttac gttgtcgcac aaagtttatt tcctagcact gtgcttgctg cttatgtttg   1020
tttggatgtg ccaacctgca gtgaccctcg tggagcctgg gtctcacgct cctcttacct   1080
agtgtgatgt gcagaaaaag tgtgatgctg taaaattatg tgattgccta gcagatgtca   1140
aattttcaat cagtagctaa ctcctttaa tggtacaggc ttgcatgatt tcatctgcaa    1200
aaaagagagg gcgggttggg tgtcaaatct agccggatgt tttcgcaagt ttgtgataaa   1260
aattgtgctg tacacttgtg tttatgcagt tgccctaggc gtcagtgggc tgaaaggtaa   1320
tatctgtgaa tt                                                       1332
```

<210> SEQ ID NO 5
<211> LENGTH: 1267
<212> TYPE: DNA
<213> ORGANISM: Zea mays

<400> SEQUENCE: 5

```
gcagagcgac gagcgacgag ctaaaccccg accgagtcgc tgcttgggtg cccaagatag      60
ccctaccgcc tcgcctctct cgttcccccct catcgccacg ccagtcgcct ccactcccag    120
tcatctccca tcaccgacga cgtgtcgagg cgagagaaga gggcgagtcc aagtctaggg    180
ttcccgccgc atcgacacgg gcatcgcacc gcaccgcgag gggcgggcac ggaggaagat    240
ggcaccgcgc gggcgcgtgg agctgcggcg gatcgaggac aaggcgagcc ggcaggtgcg    300
cttctccaag cgccgcgcgg ggctgttcaa gaaggccttc gagctggccc tgctctgcga    360
cgccgaggtc gcgctcctcg tcttttcccc cggcggcaag ctctatgagt actcctcctc    420
```

| | |
|---|---|
| cagaaccggg atgtagctgc ttcagattta cagtcgagac ttaaggagat cgcaacatgg | 480 |
| taacactaag ttttcactac tctctcccaa ctttctatgt tcaatggtgg caacaatgta | 540 |
| acaaacctgc aggtctaaac aaaacaacgc tgaggagtcg gatgccaatg aacttgagaa | 600 |
| acttgaggaa ctcctgacaa atgctttgag gaatacgaaa gccaaaaaga tgttggcaaa | 660 |
| agaaaacaat ggtggtgccg gtgcaagtac aagcagccag atgttgcttt actcggcaga | 720 |
| gcgtgcaacc gacaaatgaa acggggcgtg catctgttgc taacggggcg gtgccggtgc | 780 |
| cgcatactat tgttgtgtag ctgaggtttg tcaaggtggc tgctggcaag gttagccgag | 840 |
| gaagtggagt tcaataacag gatgcggaaa ctgtgccgct ccttgccgaa cttaagcccc | 900 |
| gttacgttgt cgcacaaagt ttatttccta gcactgtgct tgctgcttat gtttgtttgg | 960 |
| atgtgccaac ctgcagtgac cctcgtggag cctgggtctc acgctcctct tacctagtgt | 1020 |
| gatgtgcaga aaaagtgtga tgctgtaaaa ttatgtgatt gcctagcaga tgtcaaattt | 1080 |
| tcaatcagta gctaactcct tttaatggta caggcttgca tgatttcatc tgcaaaaaag | 1140 |
| agagggcggg ttgggtgtca aatctagccg gatgttttcg caagttttgtg ataaaaattg | 1200 |
| tgctgtacac ttgtgtttat gcagttgccc taggcgtcag tgggctgaaa ggtaatatct | 1260 |
| gtgaatt | 1267 |

<210> SEQ ID NO 6
<211> LENGTH: 1267
<212> TYPE: DNA
<213> ORGANISM: Zea mays

<400> SEQUENCE: 6

| | |
|---|---|
| gcagagcgac gagcgacgag ctaaaccccg accgagtcgc tgcttgggtg cccaagatag | 60 |
| ccctaccgcc tcgcctctct cgttccccct catcgccacg ccagtcgcct ccactcccag | 120 |
| tcatctccca tcaccgacga cgtgtcgagg cgagagaaga gggcgagtcc aagtctaggg | 180 |
| ttcccgccgc atcgacacgg gcatcgcacc gcaccgcgag gggcgggcac ggaggaagat | 240 |
| ggcaccgcgc gggcgcgtgg agctgcggcg gatcgaggac aaggcgagcc ggcaggtgcg | 300 |
| cttctccaag cgccgcgcgg ggctgttcaa gaaggccttc gagctggccc tgctctgcga | 360 |
| cgccgaggtc gcgctcctcg tcttttcccc cggcggcaag ctctatgagt actcctcctc | 420 |
| cagcatagaa gatacatatg accgctatca tcaatttgcg ggagcaggaa gaaaagtgaa | 480 |
| cggacataac aacgataacc gggatgtagc tgcttcagat ttacagtcga gacttaagga | 540 |
| gatcgcaaca tggtctaaac aaaacaacgc tgaggagtcg gatgccaatg aacttgagaa | 600 |
| acttgaggaa ctcctgacaa atgctttgag gaatacgaaa gccaaaaaga tgttggcaaa | 660 |
| agaaaacaat ggtggtgccg gtgcaagtac aagcagccag atgttgcttt actcggcaga | 720 |
| gcgtgcaacc gacaaatgaa acggggcgtg catctgttgc taacggggcg gtgccggtgc | 780 |
| cgcatactat tgttgtgtag ctgaggtttg tcaaggtggc tgctggcaag gttagccgag | 840 |
| gaagtggagt tcaataacag gatgcggaaa ctgtgccgct ccttgccgaa cttaagcccc | 900 |
| gttacgttgt cgcacaaagt ttatttccta gcactgtgct tgctgcttat gtttgtttgg | 960 |
| atgtgccaac ctgcagtgac cctcgtggag cctgggtctc acgctcctct tacctagtgt | 1020 |
| gatgtgcaga aaaagtgtga tgctgtaaaa ttatgtgatt gcctagcaga tgtcaaattt | 1080 |
| tcaatcagta gctaactcct tttaatggta caggcttgca tgatttcatc tgcaaaaaag | 1140 |
| agagggcggg ttgggtgtca aatctagccg gatgttttcg caagttttgtg ataaaaattg | 1200 |
| tgctgtacac ttgtgtttat gcagttgccc taggcgtcag tgggctgaaa ggtaatatct | 1260 |

```
gtgaatt                                                               1267
```

<210> SEQ ID NO 7
<211> LENGTH: 65
<212> TYPE: PRT
<213> ORGANISM: Zea mays

<400> SEQUENCE: 7

Met Ala Pro Arg Gly Arg Val Glu Leu Arg Arg Ile Glu Asp Lys Ala
1               5                   10                  15

Ser Arg Gln Val Arg Phe Ser Lys Arg Arg Ala Gly Leu Phe Lys Lys
            20                  25                  30

Ala Phe Glu Leu Ala Leu Leu Cys Asp Ala Glu Val Ala Leu Leu Val
        35                  40                  45

Phe Ser Pro Gly Gly Lys Leu Tyr Glu Tyr Ser Ser Ser Arg Thr Gly
    50                  55                  60

Met
65

<210> SEQ ID NO 8
<211> LENGTH: 65
<212> TYPE: PRT
<213> ORGANISM: Zea mays

<400> SEQUENCE: 8

Met Ala Pro Arg Gly Arg Val Glu Leu Arg Arg Ile Glu Asp Lys Ala
1               5                   10                  15

Ser Arg Gln Val Arg Phe Ser Lys Arg Arg Ala Gly Leu Phe Lys Lys
            20                  25                  30

Ala Phe Glu Leu Ala Leu Leu Cys Asp Ala Glu Val Ala Leu Leu Val
        35                  40                  45

Phe Ser Pro Gly Gly Lys Leu Tyr Glu Tyr Ser Ser Ser Arg Thr Gly
    50                  55                  60

Met
65

<210> SEQ ID NO 9
<211> LENGTH: 62
<212> TYPE: PRT
<213> ORGANISM: Zea mays

<400> SEQUENCE: 9

Met Ala Pro Arg Gly Arg Val Glu Leu Arg Arg Ile Glu Asp Lys Ala
1               5                   10                  15

Ser Arg Gln Val Arg Phe Ser Lys Arg Arg Ala Gly Leu Phe Lys Lys
            20                  25                  30

Ala Phe Glu Leu Ala Leu Leu Cys Asp Ala Glu Val Ala Leu Leu Val
        35                  40                  45

Phe Ser Pro Gly Gly Lys Leu Tyr Glu Tyr Ser Ser Ser Arg
    50                  55                  60

<210> SEQ ID NO 10
<211> LENGTH: 65
<212> TYPE: PRT
<213> ORGANISM: Zea mays

<400> SEQUENCE: 10

Met Ala Pro Arg Gly Arg Val Glu Leu Arg Arg Ile Glu Asp Lys Ala
1               5                   10                  15

```
Ser Arg Gln Val Arg Phe Ser Lys Arg Arg Ala Gly Leu Phe Lys Lys
            20                  25                  30

Ala Phe Glu Leu Ala Leu Leu Cys Asp Ala Glu Val Ala Leu Leu Val
            35                  40                  45

Phe Ser Pro Gly Gly Lys Leu Tyr Glu Tyr Ser Ser Ser Arg Thr Gly
     50                   55                  60

Met
 65

<210> SEQ ID NO 11
<211> LENGTH: 166
<212> TYPE: PRT
<213> ORGANISM: Zea mays

<400> SEQUENCE: 11

Met Ala Pro Arg Gly Arg Val Glu Leu Arg Arg Ile Glu Asp Lys Ala
 1               5                  10                  15

Ser Arg Gln Val Arg Phe Ser Lys Arg Arg Ala Gly Leu Phe Lys Lys
            20                  25                  30

Ala Phe Glu Leu Ala Leu Leu Cys Asp Ala Glu Val Ala Leu Leu Val
            35                  40                  45

Phe Ser Pro Gly Gly Lys Leu Tyr Glu Tyr Ser Ser Ser Ile Glu
     50                   55                  60

Asp Thr Tyr Asp Arg Tyr His Gln Phe Ala Gly Ala Gly Arg Lys Val
 65                  70                  75                  80

Asn Gly His Asn Asn Asp Asn Arg Asp Val Ala Ala Ser Asp Leu Gln
                 85                  90                  95

Ser Arg Leu Lys Glu Ile Ala Thr Trp Ser Lys Gln Asn Asn Ala Glu
            100                 105                 110

Glu Ser Asp Ala Asn Glu Leu Glu Lys Leu Glu Glu Leu Leu Thr Asn
        115                 120                 125

Ala Leu Arg Asn Thr Lys Ala Lys Lys Met Leu Ala Lys Glu Asn Asn
    130                 135                 140

Gly Gly Ala Gly Ala Ser Thr Ser Ser Gln Met Leu Leu Tyr Ser Ala
145                 150                 155                 160

Glu Arg Ala Thr Asp Lys
                165

<210> SEQ ID NO 12
<211> LENGTH: 219
<212> TYPE: PRT
<213> ORGANISM: Arabidopsis thaliana

<400> SEQUENCE: 12

Met Val Arg Gly Lys Thr Glu Met Lys Arg Ile Glu Asn Ala Thr Ser
 1               5                  10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Val Ile Phe
            35                  40                  45

Ser Pro Arg Ser Lys Leu Tyr Glu Phe Ser Ser Ser Ile Ala Ala
     50                   55                  60

Thr Ile Glu Arg Tyr Gln Arg Ile Lys Glu Ile Gly Asn Asn His
 65                  70                  75                  80

Lys Arg Asn Asp Asn Ser Gln Gln Ala Arg Asp Glu Thr Ser Gly Leu
                 85                  90                  95
```

```
Thr Lys Lys Ile Glu Gln Leu Glu Ile Ser Lys Arg Lys Leu Leu Gly
            100                 105                 110

Glu Gly Ile Asp Ala Cys Ser Ile Glu Glu Leu Gln Gln Leu Glu Asn
        115                 120                 125

Gln Leu Asp Arg Ser Leu Ser Arg Ile Arg Ala Lys Lys Tyr Gln Leu
    130                 135                 140

Leu Arg Glu Glu Ile Glu Lys Leu Lys Ala Glu Glu Arg Asn Leu Val
145                 150                 155                 160

Lys Glu Asn Lys Asp Leu Lys Glu Lys Trp Leu Gly Met Gly Thr Ala
                165                 170                 175

Thr Ile Ala Ser Ser Gln Ser Thr Leu Ser Ser Ser Glu Val Asn Ile
            180                 185                 190

Asp Asp Asn Met Glu Val Glu Thr Gly Leu Phe Ile Gly Pro Pro Glu
        195                 200                 205

Thr Arg Gln Ser Lys Lys Phe Pro Pro Gln Asn
    210                 215

<210> SEQ ID NO 13
<211> LENGTH: 219
<212> TYPE: PRT
<213> ORGANISM: Oryza sativa

<400> SEQUENCE: 13

Met Pro Pro Pro Pro Pro His Ser Ile Asp Pro Leu Leu Leu Leu
1               5                   10                  15

Pro His Phe Ser Pro Pro His His His Thr His Ala Arg Thr His
            20                  25                  30

Ala Arg Leu Arg Phe Pro Pro Thr Arg Gly Gly Glu Gly Gly Glu
        35                  40                  45

Leu Gly Phe Phe Gly Ala Gly Met Ala Arg Arg Gly Arg Val Gln Leu
    50                  55                  60

Arg Arg Ile Glu Asp Lys Ala Ser Arg Gln Val Arg Phe Ser Lys Arg
65                  70                  75                  80

Arg Ala Gly Leu Phe Lys Lys Ala Phe Glu Leu Ala Leu Leu Cys Asp
                85                  90                  95

Val Glu Val Ala Leu Leu Val Phe Ser Pro Val Gly Lys Leu Tyr Glu
            100                 105                 110

Tyr Ser Ser Ser Ser Ile Glu Gly Thr Tyr Asp Arg Tyr Gln Gln Phe
        115                 120                 125

Ala Gly Ala Arg Arg Asp Leu Asn Glu Gly Ser Thr Ser Ile Asn Ser
    130                 135                 140

Asp Glu Asn Ala Ser Ile His Ser Arg Leu Arg Asp Ile Thr Ala Trp
145                 150                 155                 160

Ser Leu Gln Asn Asn Ala Asp Glu Ser Asp Ala Asn Gln Leu Glu Lys
                165                 170                 175

Leu Glu Lys Leu Leu Thr Asn Ala Leu Arg Asp Thr Lys Ser Lys Lys
            180                 185                 190

Met Leu Ala Lys Gln Asn Gly Glu Gly Ser Arg Ser Arg Ala Asn Ser
        195                 200                 205

Ser Gly Ser Arg Gly Gln Glu Glu Gly Ser Ala
    210                 215

<210> SEQ ID NO 14
<211> LENGTH: 166
<212> TYPE: PRT
```

<213> ORGANISM: Brachypodium distachyon

<400> SEQUENCE: 14

Met Ala Arg Arg Gly Arg Val Glu Leu Arg Arg Ile Glu Asp Arg Thr
1               5                   10                  15

Ser Arg Gln Val Arg Phe Ser Lys Arg Arg Ala Gly Leu Phe Lys Lys
            20                  25                  30

Ala Phe Glu Leu Ala Val Leu Cys Asp Ala Glu Val Ala Leu Leu Val
        35                  40                  45

Phe Ser Pro Ala Gly Arg Leu Tyr Glu Tyr Ala Ser Ser Ile Glu
    50                  55                  60

Gly Thr Tyr Asp Arg Tyr Gln Arg Phe Ala Gly Gly Arg Trp Asn Leu
65                  70                  75                  80

Asn Asp Gly Asp Ser Ser Asn Asn Asp Glu Asp Pro Ser Asn Ile
                85                  90                  95

Gln Ser Arg Leu Gly Glu Ile Ala Ser Trp Ser Leu Gln Asn Asn Ala
            100                 105                 110

Asp Asp Ser Asp Ala Asn Lys Leu Glu Lys Leu Glu Thr Leu Leu Lys
        115                 120                 125

Asp Ala Leu Arg Asn Thr Lys Ser Lys Ile Leu Ala Lys Arg Asn Ser
130                 135                 140

Gly Ala Ser Thr Ser Gly Ser Gly Glu Asn Ser Ser Glu Pro Lys Gly
145                 150                 155                 160

Gln Glu Gly Gly Arg Ala
            165

<210> SEQ ID NO 15
<211> LENGTH: 163
<212> TYPE: PRT
<213> ORGANISM: Sorghum bicolor

<400> SEQUENCE: 15

Met Ala Arg Arg Gly Arg Val Glu Leu Arg Arg Ile Glu Asp Lys Ala
1               5                   10                  15

Ser Arg Gln Val Arg Phe Ser Lys Arg Arg Ala Gly Leu Phe Lys Lys
            20                  25                  30

Ala Phe Glu Leu Ala Leu Leu Cys Asp Ala Glu Val Ala Leu Leu Val
        35                  40                  45

Phe Ser Pro Gly Gly Lys Leu Tyr Glu Tyr Ser Ser Thr Ser Ile Glu
    50                  55                  60

Asp Thr Tyr Asp Arg Tyr Gln Gln Phe Ala Gly Ala Gly Arg Asn Val
65                  70                  75                  80

Asn Gly Asp Asn Asn Asp Asn Pro Asp Val Ala Ala Ser Asp Leu Gln
                85                  90                  95

Ser Arg Leu Lys Glu Ile Ala Thr Trp Ser Glu Gln His Asn Ala Glu
            100                 105                 110

Glu Ser Asp Ala Asn Glu Leu Glu Lys Leu Glu Lys Leu Leu Ala Asn
        115                 120                 125

Ala Leu Arg Asn Thr Lys Thr Lys Arg Met Leu Ala Lys Gln Asn Asn
130                 135                 140

Gly Gly Ala Gly Thr Ser Thr Gly Asn Gln Asn Ser Asn Gly Pro Ser
145                 150                 155                 160

Ser His Glu

<210> SEQ ID NO 16

```
<211> LENGTH: 225
<212> TYPE: PRT
<213> ORGANISM: Populus trichocarpa

<400> SEQUENCE: 16

Phe Leu Leu Trp Tyr Arg Pro Ser Gly Phe Ala Asn Leu Val Arg
1               5                   10                  15

Phe Pro Asn Leu Pro Ser Asp Phe Phe Leu Phe Thr Ser Pro Val
            20                  25                  30

Leu Tyr Glu Ser Lys Ser Thr Ser Leu Val Val Trp Leu Ala His Val
        35                  40                  45

Phe Gly Thr Asn Gln Leu His His Phe Tyr Gln Leu Lys Ser Tyr Trp
    50                  55                  60

Leu Phe Leu Gly Val Ala Phe Tyr Pro Gln Ile Ser Ser Ala Ala Ser
65                  70                  75                  80

Phe Ser Gly Phe Tyr Thr Pro Phe His Asp Gln Ser Ser Arg Gly Phe
                85                  90                  95

Ile Ala Tyr Leu His Leu Leu Ser Cys Ile Leu Lys Ser Ile His Gln
            100                 105                 110

Asp Ser Cys Phe Phe Asn Trp Val Val Trp Ser Gln Phe Ala Pro Lys
        115                 120                 125

Ala Gln Ile Phe Val Val Pro Pro Leu Ser Tyr Leu Glu Arg Arg Asn
    130                 135                 140

Leu Phe Cys Trp Val Tyr Arg Glu Met Val Arg Gly Lys Thr Gln Met
145                 150                 155                 160

Arg Arg Ile Glu Asn Ala Thr Ser Arg Gln Val Thr Phe Ser Lys Arg
                165                 170                 175

Arg Asn Gly Leu Leu Lys Lys Ala Phe Glu Leu Ser Val Leu Cys Asp
            180                 185                 190

Ala Glu Val Ala Leu Ile Val Phe Ser Pro Arg Gly Lys Leu Tyr Glu
        195                 200                 205

Phe Ala Ser Thr Arg Tyr His Leu Leu His Tyr Phe Pro Thr Phe Leu
    210                 215                 220

Pro
225

<210> SEQ ID NO 17
<211> LENGTH: 218
<212> TYPE: PRT
<213> ORGANISM: Vitis vinifera

<400> SEQUENCE: 17

Met Val Arg Gly Lys Thr Gln Met Arg Arg Ile Glu Asn Ala Thr Ser
1               5                   10                  15

Arg Gln Val Thr Phe Ser Lys Arg Arg Asn Gly Leu Phe Lys Lys Ala
            20                  25                  30

Phe Glu Leu Ser Val Leu Cys Asp Ala Glu Val Ala Leu Ile Ile Phe
        35                  40                  45

Ser Pro Arg Gly Lys Leu Tyr Glu Phe Ser Ser Ser Met Gln Glu
    50                  55                  60

Thr Ile Glu Arg Tyr Gln Arg His Thr Lys Asp Val His Thr Asn Asn
65                  70                  75                  80

Tyr Lys Thr Thr Glu His Asn Met Gln His Leu Lys His Glu Ala Ala
                85                  90                  95

Asn Met Ala Lys Lys Ile Glu Leu Leu Glu Ile Ser Lys Arg Lys Leu
            100                 105                 110
```

```
Leu Gly Glu Gly Leu Gly Ser Cys Ser Ile Glu Glu Leu Gln Gln Ile
        115                 120                 125

Glu Gln Gln Leu Glu Arg Ser Val Ser Ser Ile Arg Ala Arg Lys Asn
    130                 135                 140

Gln Val Phe Lys Glu Gln Ile Glu Gln Leu Lys Glu Lys Glu Lys Ala
145                 150                 155                 160

Leu Ala Ala Glu Asn Ala Met Leu Cys Glu Lys Cys Gly Val Gln Pro
                165                 170                 175

Tyr Gln Ala Pro Asn Gln Glu Asn Glu Thr Leu Pro Ser Ala Glu Arg
            180                 185                 190

Ser Gln Asn Ser Asp Val Ser Thr Asp Leu Phe Ile Gly Leu Pro Glu
        195                 200                 205

Gly Arg Ala Lys Arg Leu Leu Leu Gly Asn
        210                 215

<210> SEQ ID NO 18
<211> LENGTH: 2153
<212> TYPE: DNA
<213> ORGANISM: Zea mays

<400> SEQUENCE: 18
caccctcctt cctcagctcc gttgcgcacc gccaccgccg gcggccagc cgccggagca      60 ccgaaagacc cccgttcttt cctgtaaaaa aaaacccgcc gcctttagct agctaaccgg     120
tcgtcctctt cacccccctag ctttgctagc tctagctagg aacgaaagaa attaaaggat   180
aactgagatt gctgattggt ggtccgggta cggtgttctt gagtcgtgaa cgacagtac    240 agtggctagg gtcgtgccgc ccctgcagtc tccggggttg cgtgcaggat ggtcgtcagg    300
gatcgggagt gaggaggcat cagctctcgc ggtcgtggag cctaaatgta ccgcaacaac    360
gactcggcac tctcctgctt ctacctcttc ctcctctggt tcttcttctt gaagtagaca    420
ccaccagttc gccaggtagt tagcagccca gttgcgactg ggatcggtg gcgggctgcc     480 gcttgcgagt tgtaagcttg aggggaggg gagcaggagc aggagatgca gttggatctg    540
aacgtggccg aggcgccgcc gccggtggag atggaggcga cgactcggg gtcgtcggtg    600 ctgaacgcgt cggaagcggc gtcggcgggc ggcgcgcccg cgccggcgga ggagggatct    660
agctcaacgc cggccgtgct ggagttcagc atcctcatcc ggagcgatag cgacgcggcc    720
ggcgcggacg aggacgagga cgccacgcca tcgcctcctc ctcgccaccg ccaccagcac    780
cagcagcagc tcgtgacccg cgagctgttc ccggccggcg ccgtccgcc ggccccgacg     840 ccgcggcatt gggccgagct cggcttcttc cgcgccgacc tgcagcagca acaggcgccg    900
ggccccagga tcgtgccgca cccacacgcc gcgccgccgc cggccaagaa gagccgccgc    960
ggcccgcgct cccgcagctc gcagtaccgc ggcgtcacct tctaccgccg cacaggccgc   1020
tgggagtccc acatctggga ttgcggcaag caggtgtacc tagtggtggt ccggctgctg   1080
gccgatatac gcaggtggat cgacaccgc tcacgccgct gcaagggcgt acgaccgggc    1140
ggcgatcaag ttccgcggcg tcgacgccga catcaacttc aacctcagcg actacgagga   1200
cgacatgaag cagatgggga gcctgtccaa ggaggagttc gtgcacgtcc tgcgccgtca   1260
gagcaccggc ttctcgagag gcagctccag gtacagaggc gtcaccctgc acaagtgcgg   1320
ccgctgggag gcgcgcatgg ggcagttcct cggcaagaag tacatatacc ttgggctatt   1380
cgacagcgaa gtagaggctg caagagccta cgacaaggcc gccatcaaat gcaatggcag   1440
agaggccgtg acgaacttcg agccgagcac gtatcacggg gagctgccga ctgaagttgc   1500
```

| | | | |
|---|---|---|---|
| tgatgtcgat | ctgaacctga | gcatatctca | gccgagcccc caaagagaca agaacagctg | 1560 |
| cctaggtctg | cagctccacc | acggaccatt | cgagggctcc gaactgaaga aaaccaagat | 1620 |
| cgacgatgct | ccctctgagc | taccgggccg | ccctcgtcag ctgtctcctc tcgtggctga | 1680 |
| gcatccgccg | gcctggcctg | cgcagccgcc | tcacccttc ttcgtcttca caaccatga | 1740 |
| gatgagtgca | tcaggagatc | tccacaggag | gcctgcaggg gctgttccca gctgggcatg | 1800 |
| gcaggtggca | gcagcagctc | ctcctcctgc | cgccctgccg tcgtccgctg cagcatcatc | 1860 |
| aggattctcc | aacaccgcca | cgacagctgc | caccaccgcc ccatcggcct cctccctccg | 1920 |
| gtactgcccg | ccgccgccgc | cgccgtcgag | ccatcaccat cccgctgag agaatcaaga | 1980 |
| agccgcactg | taaatctgcc | gggaagctag | catttttccc ccggcccctc ccctctccg | 2040 |
| ggcgttgcga | ctttttcagt | tttgcgccgc | cggccggggt ggtggtttct tgtagccgat | 2100 |
| cgattggatt | cctcgtatta | ctgctgctta | cactcccaat taagtgaaaa aaa | 2153 |

<210> SEQ ID NO 19
<211> LENGTH: 802
<212> TYPE: DNA
<213> ORGANISM: Zea mays

<400> SEQUENCE: 19

| | | | |
|---|---|---|---|
| atgctcagac | tgcagcttcc | tcagtcccat | agggaggaag ttgagagttc taataagagc | 60 |
| aacggccaat | accattagcg | agttattttt | ctgcaatata tgtcagcaac cgatcatttg | 120 |
| gttatggctc | gtgtcataca | ggatgtattg | atcccttta caccaaccat tccactaaga | 180 |
| ataacgtaca | acaataggct | acttctgcca | agtgctgagc taaagccatc cgcggttgta | 240 |
| agtaaaccac | gagtcgatat | cggtggcagt | gacatgaggg cttctacac cctggtactg | 300 |
| attgacccgg | atgccccaag | tccaagccat | ccatcactaa gggagtactt gcactggatg | 360 |
| gtgacagata | ttccagaaac | aactagtgtc | aactttggcc aagagctaat attttatgag | 420 |
| aggccggacc | caagatctgg | catccacagg | ctggtatttg tgctgttccg tcaacttggc | 480 |
| aggggacag | tttttgcacc | agaaatgcgc | cacaacttca actgcagaag ctttgcacgg | 540 |
| caatatcacc | tcagcattgc | caccgctaca | tatttcaact gtcaagggga aggtggatcc | 600 |
| ggcggaagaa | ggtttaggga | agagtagaaa | ccataggcca ctgcatggtc acactataga | 660 |
| aatatcatca | ataatgtgca | ctatattgaa | tcaatgcacc acctctatat gctgaatgtt | 720 |
| atgtatctca | aactatgatt | gtactgactt | gaaaggttga gagcttagtc tcttagcaga | 780 |
| atatagcaca | atattactag | ta | | 802 |

<210> SEQ ID NO 20
<211> LENGTH: 1675
<212> TYPE: DNA
<213> ORGANISM: Zea mays

<400> SEQUENCE: 20

| | | | |
|---|---|---|---|
| gcttagcccg | gcggccggcc | agaactgcaa | gagagaagac caagaaacag agagagacaa | 60 |
| gcgcagggga | cagcagcggg | tagctagcta | gctagcgatc gacgacagac gatgcagatg | 120 |
| atgatgctct | ctgatctctc | gtctgacgac | cacgaggcca ctggatccag ctcctatggc | 180 |
| ggggacatgg | ccagctacgc | cctcagccct | ctcttcctcg caccggcggc ctcggccacc | 240 |
| gcgccgctgc | cgccacctcc | gcagccgccg | gccgaggagc tcaccaacaa gcaggccgcg | 300 |
| ggcggcggca | agaggaagag | aagccagccg | gggaacccag accccggcgc ggaggtgatc | 360 |

```
gcgctgtcgc cgcgcacgct ggtggcgacg aaccggttcg tgtgcgagat ctgcaacaag    420
gggttccagc gggaccagaa cctgcagctg caccgccggg gccacaacct cccctggaag    480
ctccgccagc gcagcagcct cgtcgtcccg tcgtcgtcgg cggcggcagg ctccggcggc    540
aggcagcagc agcagcaggg cgaggccgcg ccgacgccgc cgcgtaagcg cgtctacgtc    600
tgccccgagc ccacgtgcgt gcaccacgac ccggcgagag ctctggggga cttgactggg    660
atcaagaagc acttctcgcg gaagcacggg gagaagcggt ggtgctgcga gcgctgcggg    720
aagcgctacg ccgtgcagtc ggactggaag gcgcacgtca aggggtgtgg cacgcgcgag    780
taccgctgcg actgcggcat cctcttctcc aggaaggaca gcctgctcac gcacagggcc    840
ttctgcgatg ccctagcaga ggagagcgcg aggcttcttg cagcagcagc aaacaacggc    900
agcactatca ccacgaccag cagcagcaac aacaatgatc ttctcaacgc cagcaataat    960
atcacgccat tattcctccc gttcgccagc tctcctcctc ctgtcgtcgt agcggcggca   1020
caaaacccta ataacaccct cttcttcctg caccaagagc tgtccccctt cctgcaaccg   1080
agggtgacga tgcaacaaca accctcgccc tatcttgacc tccatatgca cgtcgacgcc   1140
agcatcgtca ccaccaccgg tggtctcgcg gacggcacgc cggtcagctt tggcctcgct   1200
ctggacggct cggtggccac cgtcggccac cggcgcctca ctagggactt cctcggtgtc   1260
gatggtggcg gtcgtcaggt cgaggagctg cagcttccac tgtgcgccac agcagccgca   1320
gcaggtgcca gccgcaccgc cagctgcgcc accgacctga caaggcagtg cctcggcggc   1380
cggctgccgc cggtcaacga gacctggagc cacaacttct aggcccgcta tatacttcaa   1440
gctgcattga gactttgaga gacgaatgaa cggaacaccc aaactgcatg cactctagct   1500
tgaagagcaa ccaaaactgg agtagcaagt atggtgcact actgttgtta atttaccta    1560 atttattgat ctctgttagt tctattttca tttagggcaa tgcgggctag ctaattaatt   1620
cgatgtgcac aactttgat gaatggacca gaaagtttat cttgttgctt ttttt         1675
```